US011027136B2

(12) United States Patent
Mangual-Soto et al.

(10) Patent No.: US 11,027,136 B2
(45) Date of Patent: Jun. 8, 2021

(54) SYSTEMS AND METHODS FOR AUTOMATED CAPTURE THRESHOLD TESTING AND ASSOCIATED HIS BUNDLE PACING

(71) Applicant: PACESETTER, INC., Sytlmar, CA (US)

(72) Inventors: Jan O. Mangual-Soto, Rho (IT); Wenwen Li, San Jose, CA (US); Nima Badie, Berkeley, CA (US); Luke C. McSpadden, Los Angeles, CA (US)

(73) Assignee: PACESETTER, INC., Sylmar, CA (US)

( * ) Notice: Subject to any disclaimer, the term of this patent is extended or adjusted under 35 U.S.C. 154(b) by 357 days.

(21) Appl. No.: 16/138,766

(22) Filed: Sep. 21, 2018

(65) Prior Publication Data

US 2020/0094058 A1  Mar. 26, 2020

(51) Int. Cl.
*A61N 1/368* (2006.01)
*A61N 1/362* (2006.01)
*A61N 1/365* (2006.01)
*A61N 1/37* (2006.01)
*A61B 5/349* (2021.01)

(52) U.S. Cl.
CPC ......... *A61N 1/3684* (2013.01); *A61N 1/3627* (2013.01); *A61N 1/3682* (2013.01); *A61B 5/349* (2021.01); *A61N 1/36514* (2013.01); *A61N 1/36585* (2013.01); *A61N 1/3706* (2013.01)

(58) Field of Classification Search
CPC .. A61N 1/3684; A61N 1/3627; A61N 1/3682; A61N 1/36514; A61N 1/36585; A61N 1/3706; A61N 1/371; A61N 1/3622; A61N 1/0573; A61N 1/056; A61B 5/0452
See application file for complete search history.

(56) References Cited

U.S. PATENT DOCUMENTS

2011/0264158 A1\* 10/2011 Dong .................. A61B 5/7264
607/9

\* cited by examiner

*Primary Examiner* — Mallika D Fairchild
(74) *Attorney, Agent, or Firm* — The Small Patent Law Group LLC; Dean D. Small

(57) ABSTRACT

Systems and methods for His bundle pacing using a stimulation device include applying an impulse to a His bundle of a patient heart using the stimulation device. The stimulation device then measures a response of the patient heart to application of the impulse that includes a response of a ventricle of the patient heart. The stimulation device calculates a ventricular delay as a time from application of the impulse to onset of the response of the ventricle and delivers, using a lead of the stimulation device, a backup impulse to the ventricle when at least the ventricular delay exceeds a delay value stored in a memory of the stimulation device. The stored delay may, for example, correspond to a previously determined value indicative of selective or other His bundle capture.

20 Claims, 19 Drawing Sheets

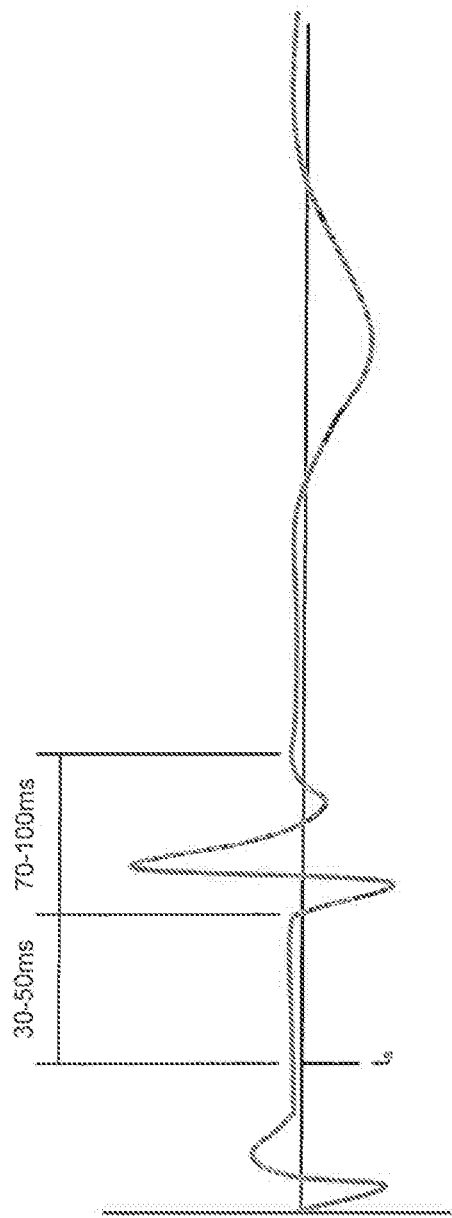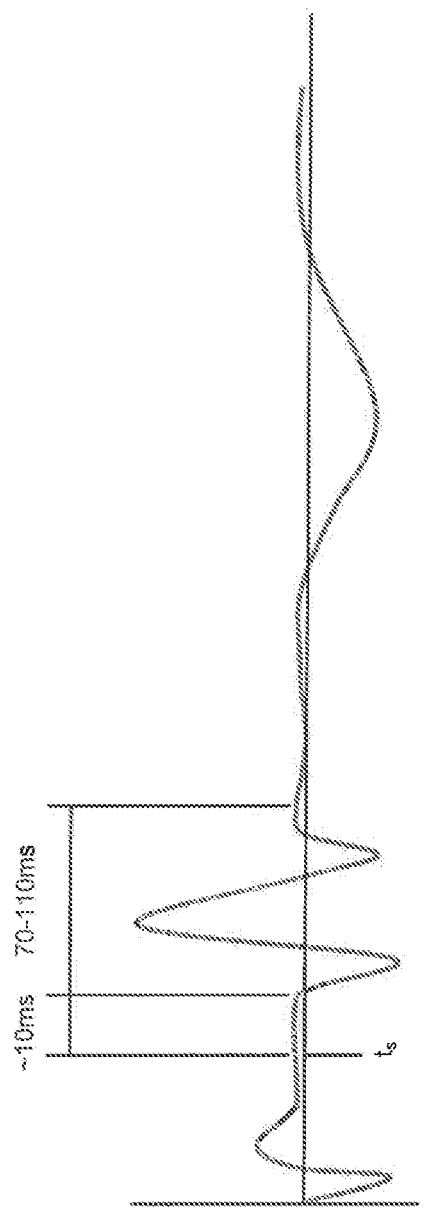

SYSTEMS AND METHODS FOR AUTOMATED CAPTURE THRESHOLD TESTING AND ASSOCIATED HIS BUNDLE PACING

FIELD

This disclosure relates generally to implantable cardiac stimulating devices. More specifically, the present disclosure is directed to a cardiac stimulation device that includes a lead for His bundle pacing and that includes logic for automatically identifying and implementing settings of the cardiac stimulation device for delivering His bundle pacing. This disclosure further relates to a method for identifying and implementing cardiac stimulating device settings for His bundle pacing.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of His (also referred to as the His bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart, via electrodes implanted in contact with the heart tissue, at a desired energy and rate. To the extent the electrical pulses are sufficient to induce depolarization of the associated heart tissue, the heart tissue is said to be captured and the minimum electrical pulse resulting in capture is generally referred to as the capture threshold.

In the majority of individuals, the most effective heartbeat is triggered by the patient's own natural pacing physiology. Implantable cardiac stimulation devices are intended to fill in when the natural pacing functionality of the patient's heart fails or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the His bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the His bundle has been found to provide hemodynamic improvement for various patients including those suffering from dilated cardiomyopathy but having normal ventricular activation. Other examples of patients that may benefit from direct stimulation of the His bundle include those with atrioventricular junction (AVJ) ablation or third-degree AV block that require permanent ventricular pacing. Accordingly, the natural conduction system, when intact, can provide hemodynamically optimal depolarization timing of the heart chambers.

What is needed, therefore, is a cardiac stimulation device capable of identifying electrical pulses for inducing His bundle capture and self-configuring output settings of the cardiac stimulation device to output such electrical pulses. To improve efficiency and operational life of the cardiac stimulation device, it would be desirable that the cardiac stimulation device identify the minimum power and rate necessary to induce His bundle capture and subsequent ventricular depolarization.

BRIEF SUMMARY OF THE DISCLOSURE

Disclosed herein are methods and systems for providing His bundle pacing of a patient heart. In one embodiment, a method of providing pacing to a patient heart using a stimulation device is provided and includes applying an impulse to a His bundle of the patient heart using the stimulation device. The stimulation device then measures a response of the patient heart to the application of the impulse, the response including a response of a ventricle of the patient heart, and calculates a ventricular delay, the ventricular delay being a time from the application of the impulse to onset of the response of the ventricle. The stimulation device then delivers, through a lead of the device, a backup impulse to the ventricle when at least the ventricular delay exceeds a delay value stored in a memory of the stimulation device.

In one implementation, the method further includes determining the response does not correspond to an ectopic beat of the patient heart and applying the backup impulse if the response does not correspond to an ectopic beat. For example, in one implementation, the lead may include multiple electrodes and the ventricular delay may be one of a plurality of ventricular delays, each of the ventricular delays measured using a respective one of the plurality of electrodes. Whether a beat is ectopic may then be determined based on a conduction order as measured by the stimulation device being different than a predetermined conduction order stored in the memory of the stimulation device. In other implementations, determining the response does not correspond to an ectopic beat of the patient heart comprises comparing the intrinsic response to a response template stored within the memory of the pacing device.

In certain implementations, method further includes determining the impulse did not result in capture of the His bundle and, in response to determining the impulse did not result in capture of the His bundle, modifying a pacing parameter of the stimulation device. The pacing parameter may be, for example, one of an amplitude, a duration, or a timing for a subsequent pacing impulse.

In another implementation, the ventricle may be a left ventricle and the response may further include a response of a right ventricle (RV) of the patient heart. In such implementations, the method may further include calculating a RV delay, the RV delay being a time from application of the impulse to onset of the response of the RV and delivering, using a RV lead of the stimulation device, a RV backup impulse to the RV when at least the RV ventricular delay exceeds a RV delay value stored in the memory of the stimulation device.

In yet another implementation, the backup impulse is delivered after a backup delay, the backup delay being less than the delay value stored in the memory of the stimulation device.

In another embodiment of the present disclosure, another method of pacing a patient heart using a stimulation device if provided. The method includes applying an impulse to a His bundle of the patient heart using the stimulation device and measuring, using the stimulation device, a response of the patient heart to application of the impulse, the response including a response of a ventricle of the patient heart. The stimulation device calculates a ventricular delay, the ventricular delay being a time from application of the impulse to onset of the response of the ventricle, and enters a backup pacing mode at least when the ventricular delay exceeds a delay value stored in the memory of the stimulation device. In the backup pacing mode a backup impulse is applied to the ventricle by the stimulation device.

In certain implementations, when in the backup pacing mode, the backup impulse is applied to the ventricle after a backup delay measured from pacing of the His bundle, the backup delay being less than the delay value stored in the memory of the stimulation device. The backup delay may be a first backup delay and at least one subsequent backup impulse may be applied to the ventricle by the stimulation device. In such cases, the subsequent backup impulse may be delivered after a second backup delay that is greater than the first backup delay.

In other implementations, entering the backup pacing mode further requires determining the response of the ventricle does not correspond to an ectopic beat.

In yet another embodiment of the present disclosure, a stimulation device for use in applying His bundle pacing of a patient heart is provided. The stimulation device includes a housing containing a memory and a controller, a His bundle lead coupleable to each of the housing and the patient heart and a His bundle of the patient heart, and a ventricular lead coupleable to each of the housing and a ventricle of the patient heart. The controller is configured to apply, through the His bundle lead, a pacing impulse to the His bundle and to measure, using the ventricular lead, a response of the patient heart to application of the Impulse, the response including a response of the ventricle. The controller is further configured to calculate a ventricular delay, the ventricular delay being a time from application of the pacing impulse to onset of the response of the ventricle and to apply, using the ventricular lead, a backup impulse to the ventricle when at least the ventricular delay exceeds a delay value stored in the memory.

In certain implementations, the ventricular lead is a left ventricle (LV) lead, the ventricle is a LV of the patient heart, and the stimulation device further includes a right ventricle (RV) lead. In such implementations, the controller may be further configured to measure, using the RV lead, the response of the patient heart to application of the impulse, the response including a response of the RV and to calculate an RV delay, the RV delay being a time from application of the pacing impulse to onset of the response of the RV. The controller may be further configured to apply, using the RV lead, a RV backup impulse to the RV when at least the RV delay exceeds a RV delay value stored in the memory.

The controller may be further configured to determine the response does not correspond to an ectopic beat of the patient heart and to apply the backup impulse if the response does not correspond to an ectopic beat.

In certain implementations, the ventricular lead may include a plurality of electrodes and the ventricular delay may be one of a plurality of ventricular delays, each of the ventricular delays measured using a respective one of the plurality of electrodes. In such implementations, the controller may further determine an activation order of the plurality of electrodes.

The controller may also be configured to determine the impulse did not result in capture of the His bundle and, in response to determining the impulse did not result in capture of the His bundle, automatically modify a pacing parameter for a subsequent impulse applied to the His bundle.

In certain implementations, the controller is configured to apply the backup impulse after a backup delay, the backup delay being less than the delay value stored in the memory of the stimulation device. In such implementations, the controller may be further configured to apply one or more subsequent backup impulses after the backup delay and to increase the backup delay between backup impulses until the backup delay exceeds the delay value stored in the memory of the stimulation device.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIGS. 1A and 1B are example electrocardiograms illustrating selective and non-selective His bundle capture, respectively;

DETAILED DESCRIPTION

Figure 2:
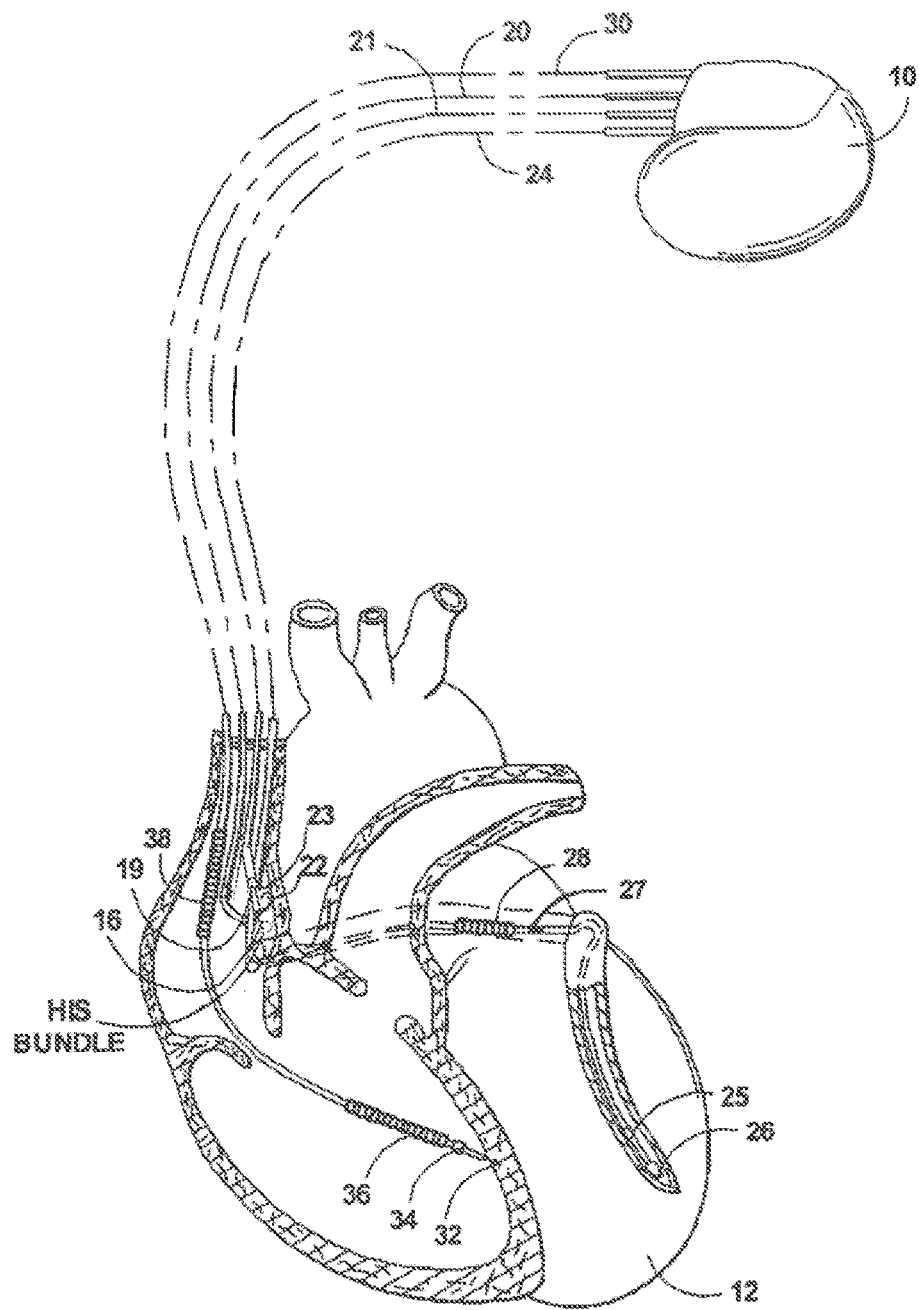
FIG. 2 is a simplified, partly cutaway view illustrating an implantable stimulation device in electrical communication with at least four leads, including a His Bundle lead, implanted into a patient's heart for delivering multi-chamber stimulation and shock therapy.

A. Overview of Cardiac Stimulation Devices and Associated Components

The present disclosure is directed at providing a method and apparatus for automatic determination of His bundle capture thresholds and for configuring stimulation devices based on the determined capture thresholds. One embodiment of the present disclosure may be implemented in either a dual chamber or multi-chamber cardiac stimulation device. For example, the present disclosure may be implemented in a rate-responsive multi-chamber cardiac stimulation device such as the stimulation device 10 depicted in FIG. 2.

Certain cardiac pacemakers and defibrillators incorporate a pacing lead in the right ventricle and may also include a second lead in the right atrium. High-burden right ventricle pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. His bundle pacing (HBP) may restore physiological activation patterns by utilizing a patient's intrinsic conduction system and may do so even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown most effective for patients exhibiting a wide QRS complex and left bundle branch block. HBP has also been shown to be effective at narrowing the QRS complex in patients with left bundle branch block, likely due to the anatomy of the His bundle, which includes right and left bundle fibers that are longitudinally dissociated. Therefore, what is thought of as left bundle branch block, can be a result of a proximal blockage within the His bundle that eventually branches to the left bundle. As a result, by pacing the His bundle distal to the blockage, a normalized QRS complex can be achieved in some patients. Theoretically, this pacing mode may provide even better results than known CRT treatments, as activation propagates rapidly through natural conduction pathways.

The His bundle is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the His bundle and a subsequent depolarization of the ventricles in response to the excitation is generally on the order of approximately 30-50 milliseconds (ms) and the resulting QRS complex generally has a duration of approximately 70-100 ms.

Depending on electrode position, pacing leads targeted for the His bundle may achieve either non-selective or selective HBP. Non-selective His bundle pacing (nsHBP) refers to pacing of the His bundle in which both the His bundle and the local myocardium surrounding the His bundle are captured. Capture occurs when an electrical stimulus applied to the heart is of sufficient energy to depolarize the cardiac tissue, thereby causing the heart muscle to contract. As a result of the simultaneous depolarization of multiple areas of cardiac tissue, the sequential electrical responses typically observed during normal heart activity may be combined or condensed. His bundle capture resulting in such a response is often characterized by the stimulus to ventricular depolarization duration being short, on the order of 20 ms, because the myocardial depolarization propagates immediately without exclusively traveling through the His-Purkinje system. Because the His bundle is stimulated, the QRS duration is similar to the native QRS duration but may be slightly longer due to the myocardial excitation (e.g., 70-120 ms). In contrast, selective His bundle pacing (sHBP) refers to exclusive capture of the His bundle without stimulating surrounding myocardial tissue. With sHBP, the stimulus to ventricular depolarization interval is virtually the same as the native delay between His bundle stimulation and subsequent ventricular depolarization and the QRS duration is essentially identical to the native QRS duration.

To further illustrate the foregoing, FIGS. 1A and 1B are example electrocardiograms corresponding to selective and non-selective His bundle capture, respectively. In each of FIGS. 1A and 18, a stimulus is applied at a predetermined time ($t_s$) following an atrial event. In FIG. 1A, selective His bundle capture occurs, i.e., only the His bundle is captured and the myocardium is not excited by the stimulus applied at $t_s$. As a result, the delay between application of the stimulus and initiation of the QRS complex is generally in the range of approximately 30 to 50 ms, which is generally consistent with normal heart function. The resulting QRS may be narrowed, but is typically between 70 and 100 ms in duration. The example electrocardiogram of FIG. 1B, in contrast, illustrates non-selective His bundle capture in which the stimulus applied at $t_s$ results in simultaneous capture of both the His bundle and the myocardium. With non-selective capture the delay between application of the stimulus and the initiation of the QRS complex is reduced (typically less than 10 ms) and the QRS duration generally remains between 70 and 120 ms.

Because sHBP more closely approximates native heart function, it is generally preferred to nsHBP. However, due to the complexity and dynamic nature of certain cardiomyopathies and cardiac anatomies, sHBP may not be possible or, if possible at one time, may no longer be possible as a patient's condition changes. Moreover, a patient's condition may also change to the point where HBP is generally unsuitable as a pacing method and ventricular pacing is required.

Figure 11:
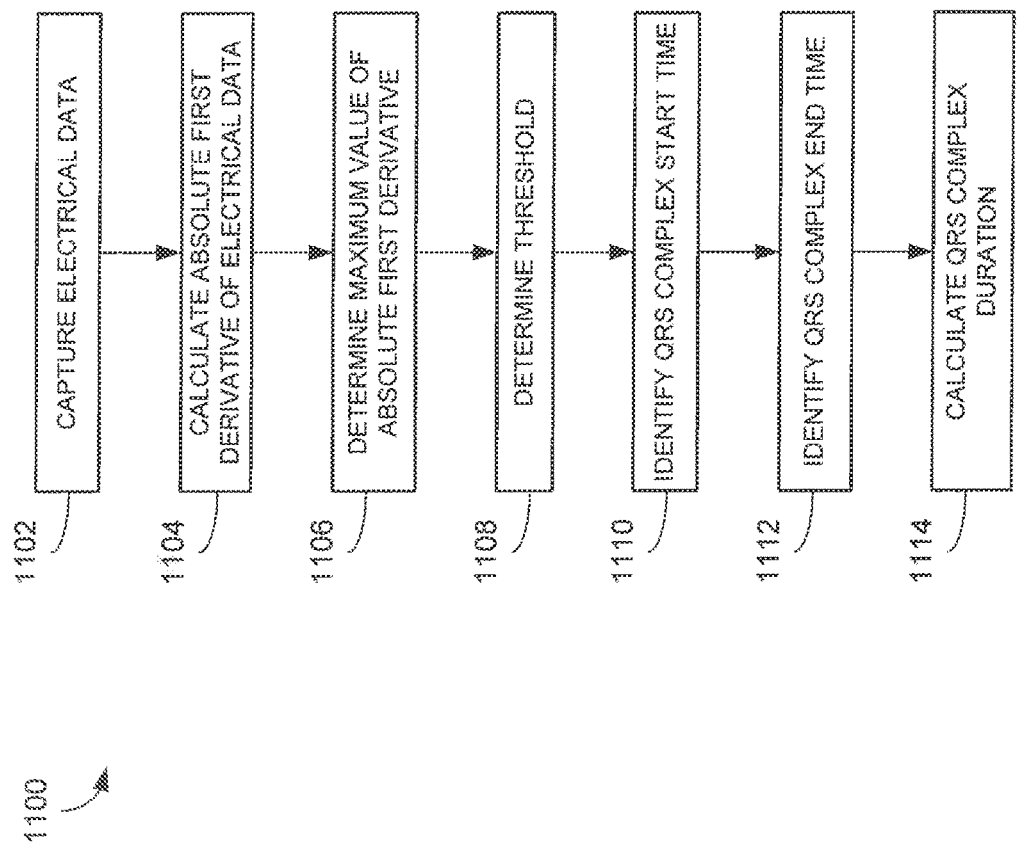
FIG. 11 is a flow chart illustrating a method for determining QRS complex duration.
Figure 12:
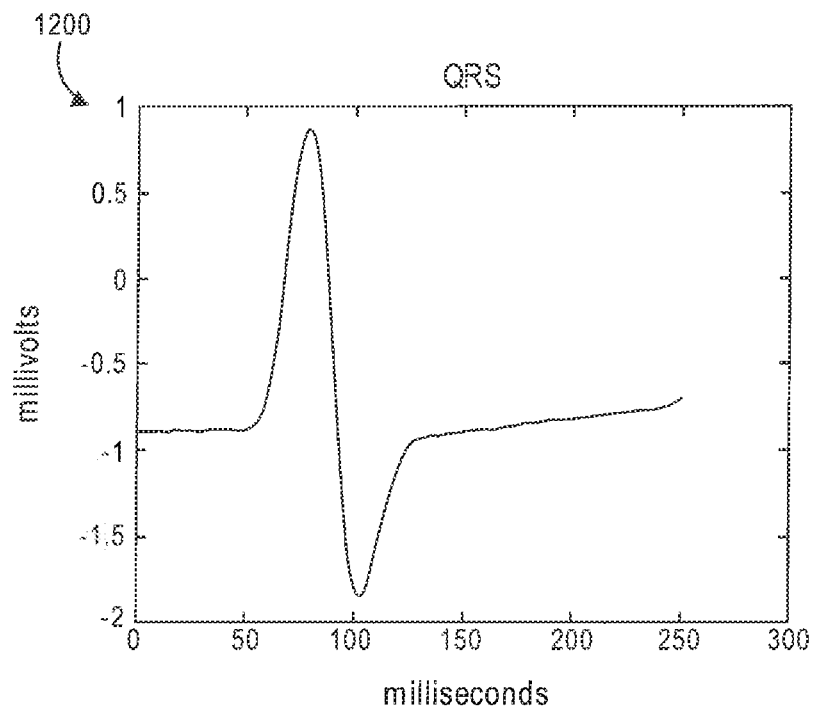
FIGS. 12 and 13 are graphs of example electrical data for illustrating the method of FIG. 11.
Figure 13:
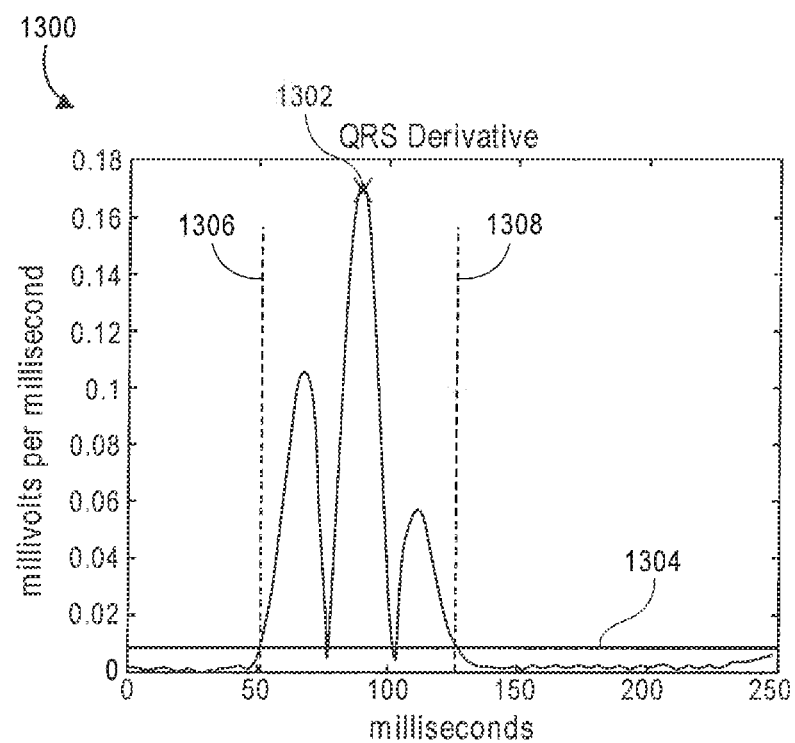

In light of the foregoing, this disclosure describes methods and apparatuses directed to optimizing HBP of a patient's heart. More specifically, this disclosure describes stimulation devices capable of HBP and processes that may be implemented by such stimulation devices to initialize and dynamically modify settings of the stimulation devices to provide HBP. To do so, the stimulation devices are generally capable of identifying and dynamically modifying one or more capture thresholds associated with HBP. As discussed below in more details, FIGS. 2-7 generally describe the components and functionality of stimulation devices in accordance with this disclosure while FIGS. 8A-10 illustrate various processes that may be implemented by such stimulation devices to provide HBP. FIGS. 11-13 illustrate a method for determining QRS duration in accordance with this disclosure as may be used during the methods of FIGS. 8A-10.

With reference to FIG. 2, the stimulation device 10 is shown in electrical communication with a patient's heart 12 by way of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a His bundle lead 21 having a His tip electrode 16, such as a helical active fixation device, and a His ring electrode 19 located proximal from the His tip electrode 16. In certain implementations, the His ring electrode 19 is located approximately 10 mm proximal the His tip electrode 16. The His bundle lead 21 may be transvenously inserted into the heart 12 so that the His tip electrode 16 is positioned in the tissue of the His bundle. Accordingly, the His bundle lead 21 is capable of receiving depolarization signals propagated in the His bundle or delivering stimulation to the His bundle, creating a depolarization that can be propagated through the lower conductive pathways of the right and left ventricles (i.e., the right and left bundle branches and Purkinje fibers).

The His bundle lead 21 will be described in greater detail in conjunction with FIGS. 5 and 6.

Figure 3:
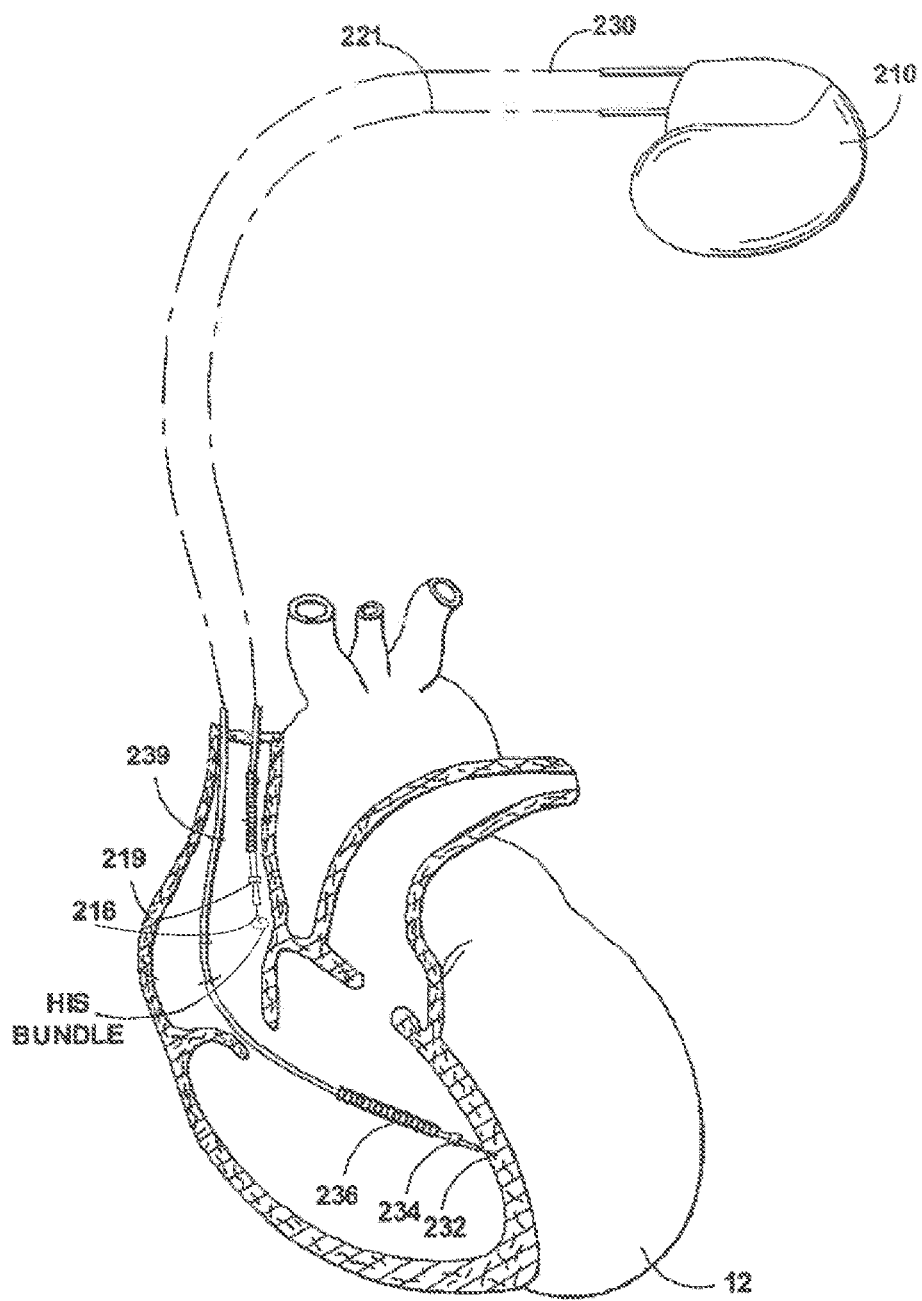
FIG. 3 is a simplified, partly cutaway view illustrating an alternative design of an implantable stimulation device, shown implanted into the right chambers of the patient's heart for delivering dual-chamber stimulation and shock therapy.

An alternative embodiment of the present disclosure is shown in FIG. 3 in which a dual chamber stimulation device 210 is in communication with one atrium, one ventricle, and the His bundle. Though not explicitly illustrated in FIG. 3, a right atrial lead 20 (shown in FIG. 2) can be optionally included. In such implementations, the stimulation device 210 maintains communication with the right atrium of the heart 12 via a right atrial lead 20 having at least an atrial tip electrode 22 and an atrial ring electrode 23 (which may be implanted in the patient's right atrial appendage as described earlier in connection with FIG. 2), and an SVC coil electrode 239.

A His bundle lead 221, having a His tip electrode 216 and a His ring electrode 219, is positioned such that the His tip electrode 216 is proximate the His bundle tissue. The stimulation device 210 is shown in FIG. 3 in electrical communication with the patient's heart 12 by way of a right ventricular lead 230 including a right ventricular tip electrode 232, a right ventricular ring electrode 234, and a right ventricular coil electrode 236.

Figure 4:
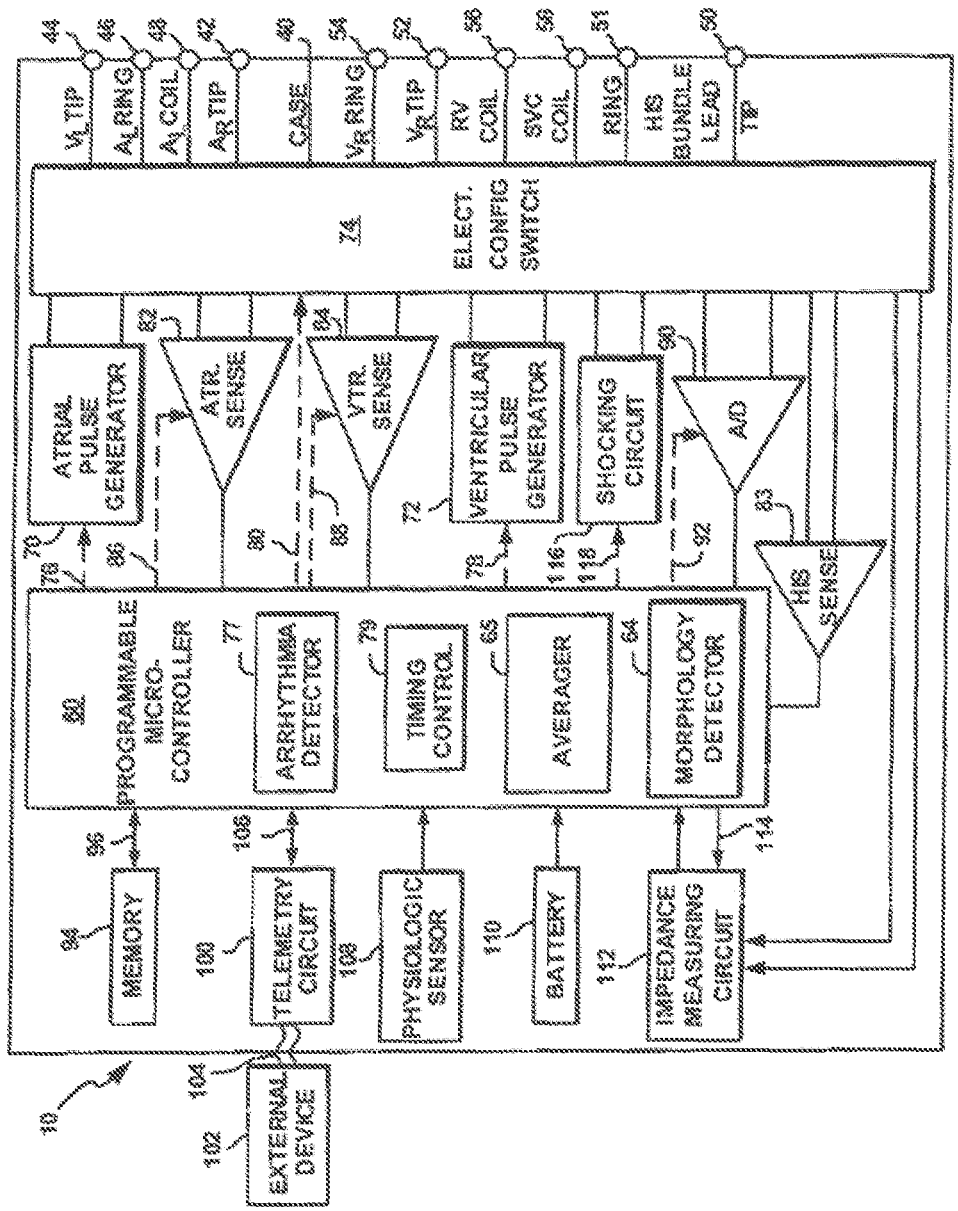
FIG. 4 is a functional block diagram of the multi-chamber implantable stimulation device of FIG. 2, illustrating the basic elements that provide pacing stimulation, cardioversion, and defibrillation in four chambers of the heart.

Referring now to FIG. 4, there is illustrated a simplified block diagram of the multi-chamber implantable stimulation device 10 of FIG. 2, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 4, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 2) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 2).

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively (each shown in FIG. 2).

To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 2).

To achieve His bundle sensing, or sensing and stimulation, the connector further includes a His bundle lead tip terminal 50 and a His bundle lead ring terminal 51 which are adapted for connection to the His tip electrode 16 and the His ring electrode 19, respectively (each shown in FIG. 2).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 4, an atrial pulse generator 70 and a ventricular pulse generator 72 generate pacing stimulation pulses for delivery by the right atrial lead 20, the right ventricular lead 30, the coronary sinus lead 24, and/or the His bundle lead 21 via an electrode configuration switch 74. It is understood that in order to provide stimulation therapy in each of the four chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present disclosure, timing control circuitry 79 also controls the onset and duration of a His signal sensing window during which a depolarization signal conducted through the AV node to the His bundle can be detected. Timing control circuitry 79 also controls a timing delay provided after a detected His signal detection, prior to the delivery of a right and/or left ventricular stimulation pulse.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one embodiment of the present disclosure, a His sensing circuit 83 is selectively coupled to the His bundle lead 21 (shown in FIG. 2) for detecting the presence of a conducted depolarization arising in the atria and conducted to the His bundle via the AV node. As used herein, each of the atrial sensing circuit 82, the ventricular sensing circuit 84, and the His sensing circuit 83, includes a discriminator, which is a circuit that senses and can indicate or discriminate the origin of a cardiac signal in each of the cardiac chambers.

Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart.

The atrial and ventricular sensing circuits 82, 84, in turn, receive control signals over signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90 represented by an A/D converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the His bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the His bundle signal. In one embodiment, an averager 65 is used to determine a sliding average of the His bundle signal during a His signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed at least once a day during at least the acute phase (e.g., the first 30 days following device implant) and less frequently thereafter. A capture threshold search would begin at a desired starting point (either a high energy level or the level at which capture is currently occurring) and decrease the energy level until capture is lost. The minimum energy at which capture is consistently obtained is known as the capture threshold. Thereafter, a safety margin can be automatically or programmably added to the capture threshold.

Capture detection and threshold testing may also be performed for purposes of His bundle pacing. The process of performing capture threshold testing for His bundle pacing and configuring the stimulation device 10 based on the results of such testing are described in more detail below in the context of FIGS. 8A, 8B, and 9.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 10 additionally includes a battery 110 which provides operating power to all of the circuits shown in FIG. 4. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The device 10 is shown in FIG. 4 as having an impedance measuring circuit 112 which is enabled by the microcontroller 60 via a control signal 114. The known uses for an impedance measuring circuit 112 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

According to one embodiment of the present disclosure, the His tip electrode 16 and His ring electrode 19 may be selectively coupled via switch 74 to the impedance measuring circuit 112 for performing a tissue impedance measurement. The tissue impedance measurement may be made to determine the location of the His bundle as the His tip electrode 16 or mapping collar 418 as shown in FIG. 5, or sensing electrodes 520-523 (shown in FIG. 6) are advanced along the endocardial surface of the right atrium. A method for performing this tissue impedance measurement using the His bundle lead 21 will be described further in conjunction with FIG. 7.

In the case where the stimulation device 10 is intended to operate as an implantable cardioverter/defibrillator (ICD)

device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 5:
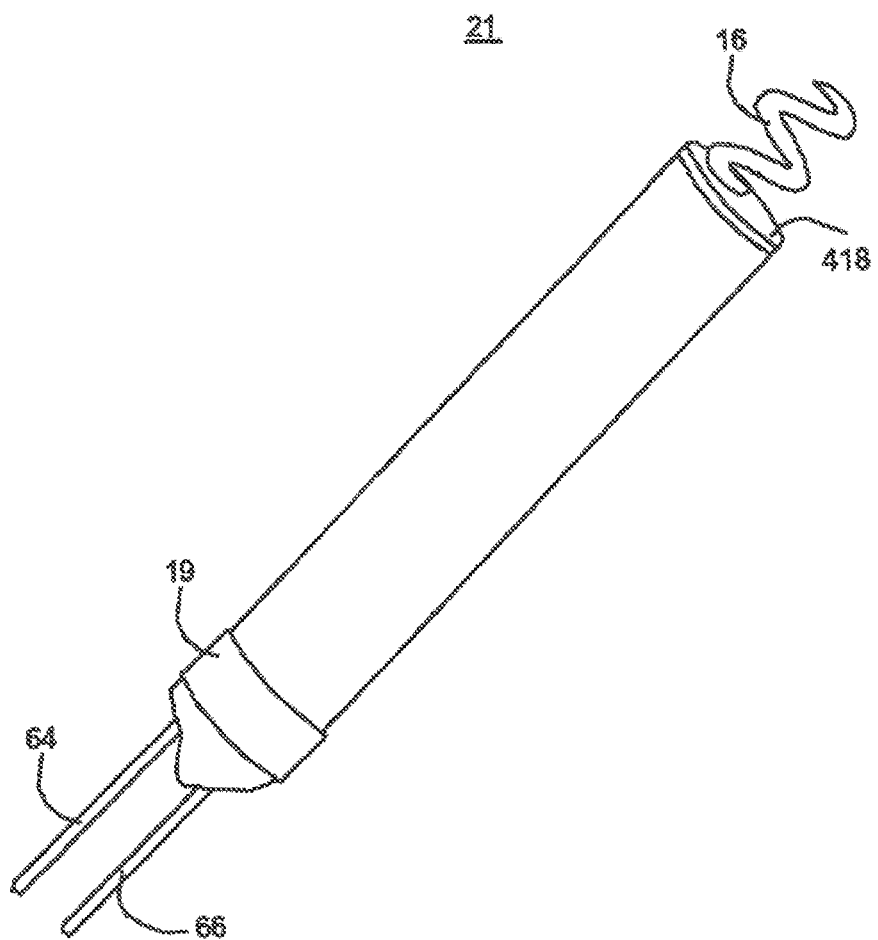
FIG. 5 is a partly fragmentary illustration of the distal end of the His bundle lead for use with the stimulation device of FIG. 4, depicting a tip electrode with an active fixation device and a non-traumatic conductive surface, and a ring electrode.

A more detailed illustration of the His bundle lead 21 is shown in FIG. 5. At the distal end of the lead 21 is the His bundle tip electrode 16. The His bundle tip electrode 16 is, or includes, an active fixation device, such as a helical, "screw-in," device that allows stable fixation of the electrode in the His bundle tissue.

The distal end of the His bundle lead 21 is further provided with a non-traumatic conductive surface (also referred to herein interchangeably as a mapping collar) 418. The non-traumatic conductive surface 418 is advantageously used to make electrical measurements that indicate the location of the His bundle without having to anchor the His bundle tip electrode 16 into the endocardial tissue. The non-traumatic conductive surface 418 and the His bundle tip electrode 16 are electrically coupled within the lead body of the His bundle lead 21 and together form one conductive element for the purposes of sensing, stimulation, and impedance measurements. Drugs, for example an acute anti-arrhythmic drug such as lidocaine and/or an anti-inflammatory agent such as dexamethazone sodium phosphate, can be stored, for example, within a reservoir (not shown) at the base of the His bundle tip electrode 16 for local dispensation.

The His bundle lead 21 is also provided with a His ring electrode 19. The His ring electrode 19 is preferably spaced between approximately 2 mm and 30 mm, but preferably 10 mm, from the His tip electrode 16. The His ring electrode 19 may function as the return electrode during bipolar sensing, stimulation or impedance measurement operations.

The His tip electrode 16 and the His ring electrode 19 are each connected to flexible conductors 64, 66, respectively, which may run the entire length of the His bundle lead 21. The flexible conductor 64 is connected to the His tip electrode 16 and is electrically insulated from the flexible conductor 66 by a layer of insulation. The conductor 66 is connected to the His ring electrode 19. The flexible conductors 64, 66 serve to electrically couple the His ring electrode 19 and the His tip electrode 16 to the His ring terminal 51 and the His tip electrode terminal 50, respectively. One embodiment of the His bundle lead 21 is available from St. Jude Medical CRMD as lead model No. 1488T.

Figure 6:
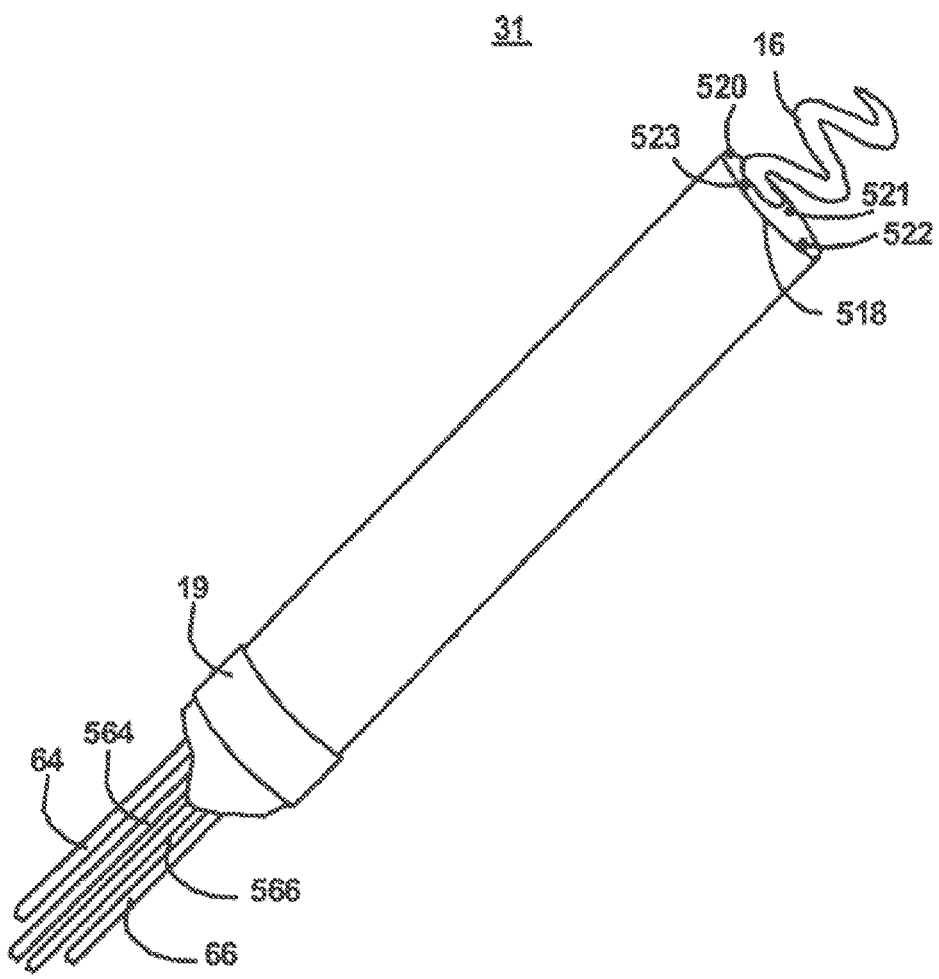
FIG. 6 is a partly fragmentary illustration of the distal end of another His bundle lead for use with the stimulation device of FIG. 4, depicting a tip electrode with an active fixation device and a non-traumatic conductive surface, a ring electrode, and four conductive sensing electrodes.

FIG. 6 illustrates an alternative His lead 31 that is generally similar in function and design to the His lead 21 shown in FIG. 5. The His lead 31 is provided with a His tip electrode 16 that includes multiple, round, closely-spaced conductive surfaces 520-523 that are arranged on a distal face 518 of the lead 31, directly facing the His bundle tissue. Though four round conductive surfaces 520-523 are shown as being uniformly distributed around the His tip electrode 16 and are electrically separated from each other by insulating material, it should be clear that a different number of conductive surfaces may alternatively be selected.

In one embodiment, a conductive surface, e.g. 520 is connected to a flexible conductor, e.g. 564 that extends along the length of the His bundle lead 31. The remaining conductive surfaces 521-523 are electrically connected together and are also connected to a flexible conductor 566 that extends along the length of the His bundle lead 31. The flexible conductors, e.g. 564, 566 are insulated from each other.

In the embodiment of FIG. 6 and with reference to FIG. 4, the device 10 includes two separate connection terminals, one for each of the two flexible conductors 564, 566 that are further connected to switch 74. The two flexible conductors 564, 566 can then be selectively connected as desired to the His sensing circuit 83, ventricular pulse generator 72, or impedance measuring circuit 112 for sensing, stimulating, and measuring tissue impedance at the site of the His bundle.

Using the lead 31, it is possible to effect stimulation with the His tip electrode 16 and the His ring electrode 19, and to effect sensing with the conductive surfaces 520-523. According to another design, the sensing is effected by the conductive surfaces 520-523 and stimulation is effected by means of the leads other than the His lead 31, for example the right atrial lead 20. For more details regarding a heart electrode equipped with multiple conductive surfaces, reference is made to U.S. Pat. Nos. 5,306,292 and 5,645,580, which are incorporated herein by reference.

During the implantation procedure, the His bundle lead 21 of FIG. 5 (or the His bundle lead 31 of FIG. 6) is introduced transvenously into the right atrium. It is then gradually advanced with the His tip electrode 16 in contact with the endocardial tissue. Electrical measurements may be made continuously as the His tip electrode 16 is advanced to determine the location of the His bundle. The non-traumatic conductive surface 418 advantageously provides electrical contact with the endocardial tissue thereby allowing electrical measurements to be performed without having to fix the His tip electrode 16 into the endocardial tissue using the His bundle tip electrode 16.

Figure 7:
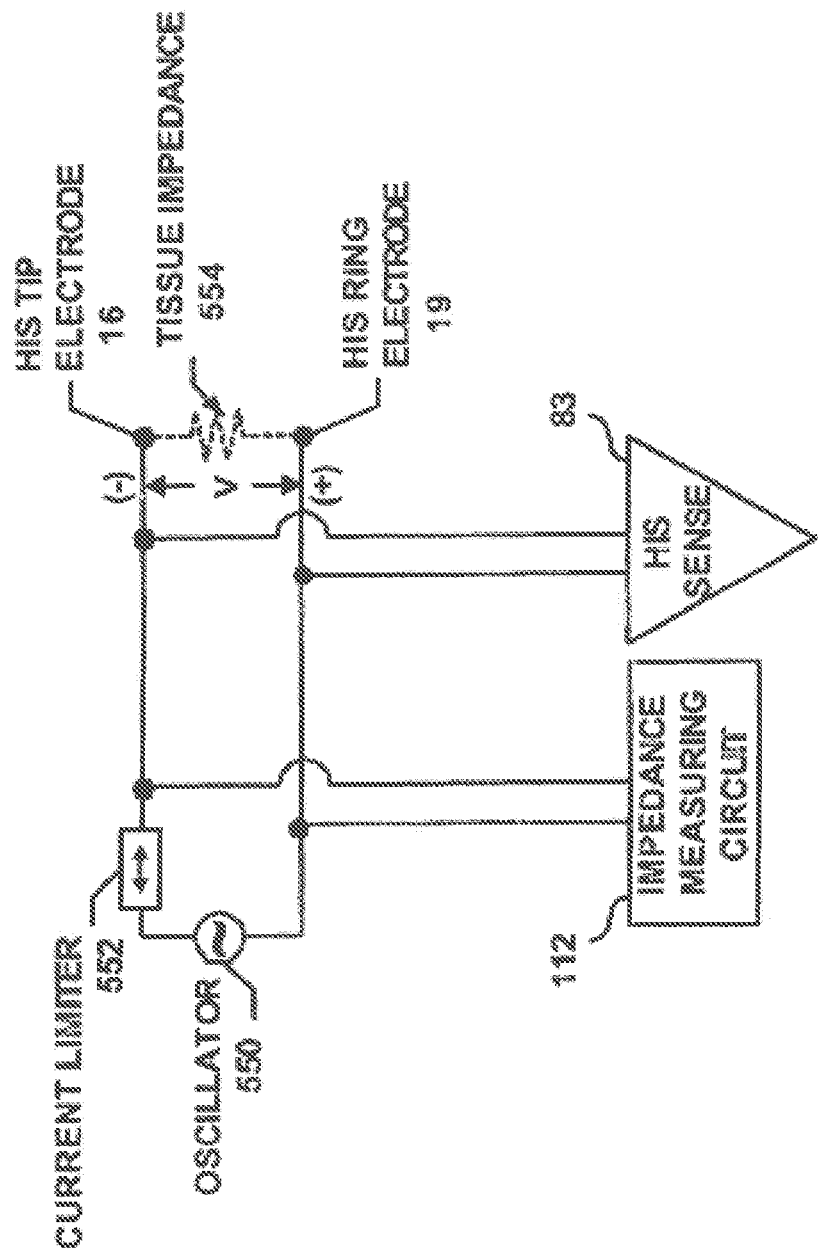
FIG. 7 is an equivalent circuit diagram illustrating a tissue impedance measurement method using the lead of FIG. 5 and the stimulation device of FIG. 4 for locating the His Bundle.

In one embodiment, tissue impedance measurements are made in order to locate the His bundle. The equivalent circuit diagram depicted in FIG. 7 represents a model by which a tissue impedance measurement can be made using the His bundle lead 21 of FIG. 5. An excitation current is applied through the His tip electrode 16. The excitation current is preferably provided as a current limited high-frequency alternating current signal produced by a 30 kHz oscillator 550 passing through a current limiter 552. A voltage signal can then be measured between the His tip electrode 16 (or the non-traumatic conductive surface 418) and the His ring electrode 19 in a bipolar fashion. The voltage signal is related to the supplied current and the tissue impedance 554 associated with the tissue in contact with the His tip electrode 16. Thus, the measured voltage signal is processed by the impedance measuring circuit 112 to determine the impedance of the tissue in contact with His tip electrode 16. The impedance equals the voltage divided by the current.

Right atrial tissue impedance is expected to be approximately twice that of the His bundle. Using the foregoing measurement method, the right atrial tissue impedance is typically on the order of 1200-1500 ohms, whereas the His bundle tissue impedance is typically on the order of 600-800 ohms. Other impedance values can be obtained using different measurement techniques. Thus, as the His bundle lead 21 is advanced in the right atrium, a large decrease in measured tissue impedance 554, of approximately 50%, indicates that the His bundle tip electrode 16 is proximate the His bundle.

The His tip electrode 16 may then be secured in the His bundle thereby anchoring the His tip electrode 16 in contact with the His bundle tissue. The electrogram signal arising from the His bundle can then be received by the His sensing circuit 83. A bypass filter (not shown) that allows signals ranging from 30-200 Hz to be received may be used to block the high frequency alternating current excitation signal produced by the oscillator 550.

B. His Bundle Capture Threshold Testing

Stimulation devices in accordance with this disclosure may be configured to perform a capture threshold test to classify electrical impulses generated by the stimulation device based on characteristics of the response elicited by applying the electrical impulses to a patient's heart. Based on the classification, the stimulation device may then initiate and/or adjust its settings to provide optimal HBP.

Figure 8A:
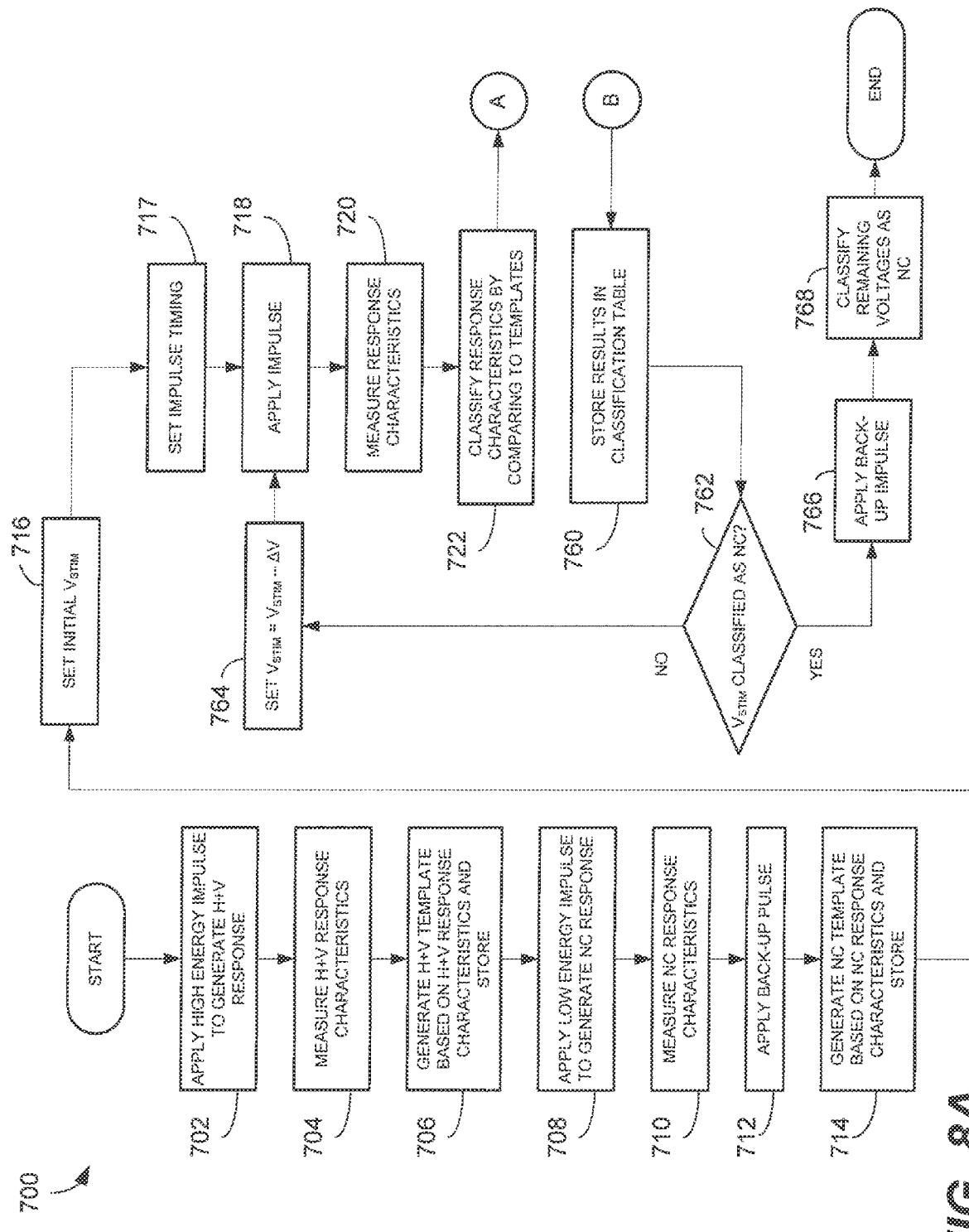
FIGS. 8A and 8B are a flow chart illustrating a method of performing a capture threshold test that may be implemented using the stimulation device of FIG. 2.
Figure 8B:
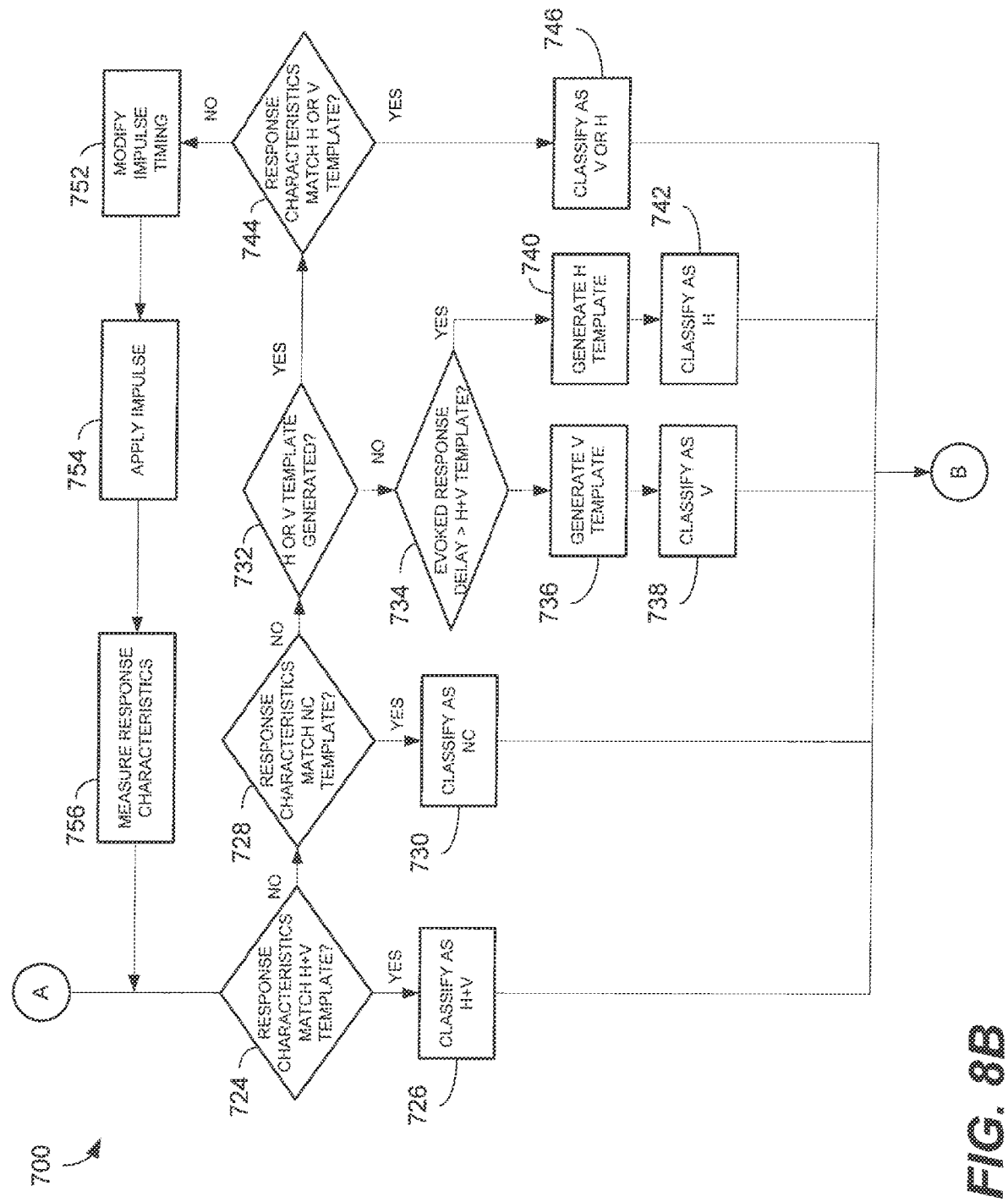

FIGS. 8A-8B include a flow chart illustrating a method 700 for conducting a capture threshold test using a stimulation device, such as the stimulation device 10 of FIG. 4. The capture threshold test comprises applying a series of electrical impulses to the His bundle via a His tip electrode, such as the His tip electrode 16, and classifying the electrical impulses based on characteristics of the response of the heart tissue to the electrical impulse. Such response characteristics may be analyzed to determine if the applied electrical impulse resulted in capture of one or more of the His bundle and the right ventricle. In certain implementations, the capture threshold test illustrated in FIGS. 8A-8B may be conducted manually by a physician, technician, or similar medical personnel that issues commands to the stimulation device 10, for example through the telemetry circuit 100 (shown in FIG. 4). In other embodiments, the capture threshold test may be implemented as a series of instructions stored within the memory 94 of the stimulation device 10 and executable by the programmable micro-controller 60 (also shown in FIG. 4).

Manual and automatic capture threshold testing may be performed at various times. For example, either of manual and automatic capture threshold testing in accordance with FIGS. 8A-8B may be performed as part of one or more of implantation, implantation follow-up, and troubleshooting of the stimulation device 10. Automatic capture threshold testing may also be performed by the stimulation device 10 according to a predetermined schedule. For example, in certain implementations, automatic capture threshold testing may be performed by the stimulation device 10 at a regular frequency during times when the patient is asleep or otherwise inactive, such as on a daily basis during the late evening or early morning. The stimulation device 10 may also initiate automatic capture threshold testing in response to detecting specific events. For example, during regular operation, the stimulation device 10 may measure response characteristics of impulses delivered by the stimulation device 10 to determine whether the current settings result in His bundle capture. If not, the stimulation device 10 may initiate or schedule an automatic capture threshold test.

As discussed below in more detail below, the method 700 generally includes applying an impulse having a predetermined voltage and duration using the stimulation device 10, measuring response characteristics of the heart, and determining whether the response characteristics indicate capture of one, both, or neither of the His bundle and right ventricle. The response characteristics may include, without limitation, the time between application of the impulse and initiation of a corresponding QRS complex (referred to herein as the "evoked response delay") and the duration of the induced QRS complex. In certain implementations, the stimulation device 10 may generate and store one or more templates including values or ranges of values for response characteristics that are indicative of particular cardiac tissue being captured. For example, the stimulation device 10 may store templates corresponding to one or more of non-selective HBP (an "H+V" template), selective HBP (an "H" template), capture of the right ventricle only (a "V" template), and non-capture of either the His bundle or right ventricle (an "NC" template).

Performing capture threshold testing generally includes each of sensing and pacing of heart tissues. For the purposes of the method 700, sensing includes sensing electrical activity of each of the His bundle and the right ventricle. Such sensing may be accomplished using various electrode configurations and sensing vectors. Referring to FIG. 2, sensing vectors that may be used to measure electrical responses for the purposes of capture threshold testing may include, without limitation, those extending between the following pairs of electrodes: (i) the atrial tip electrode 22 and the stimulation device 10; (ii) the right atrial ring electrode 23 and the stimulation device 10; (iii) the right atrial tip electrode 22 and the right atrial ring electrode 23; (iv) the right ventricle coil electrode 36 and the stimulation device 10; (v) the SVC electrode 38 and the stimulation device 10; and (vi) the right ventricle coil electrode 36 and the SVC electrode 38. In implementations in which a left ventricular lead is present, additional possible sensing vectors include those extending between: (i) the right ventricle coil electrode 36 and a coil electrode of the left ventricular lead; (ii) the SVC coil electrode 38 and the left ventricle coil electrode; and (iii) the right ventricular tip electrode 32 and a ventricular tip electrode of the left ventricular lead. Similarly, application of pacing impulses to the His bundle may be accomplished in various ways depending on the particular configuration of the pacemaker or defibrillation device. For example, His bundle pacing may be achieved along a vector defined between any of the following pairs of electrodes: (i) the His tip electrode 16 and the stimulation device 10; (ii) the His ring electrode 19 and the stimulation device 10; and (iii) the His tip electrode 16 and the His ring electrode 19.

Referring now to FIG. 8A, the method 700 includes first generating each of an H+V template and an NC template, corresponding to non-selective His bundle capture and non-capture, respectively. Generation of the H+V template may include applying a high energy impulse predetermined to induce non-selective His bundle capture (operation 702), measuring characteristics of the corresponding response (operation 704), and generating and storing an H+V template based on the measured response characteristics (operation 706). As previously noted, the H+V template may include values or ranges of values corresponding to each of an evoked response delay and a QRS complex duration.

A similar series of steps may also be performed to generate the NC template. More specifically, a low energy impulse predetermined not to induce capture of either the His bundle or right ventricle may be applied (operation 708) and the resulting response characteristics may be measured (operation 710). A back-up impulse may then be applied (operation 712). The back-up impulse is generally of a sufficient voltage and duration to capture at least the right ventricle, thereby facilitating beating of the heart despite the lack of capture during application of the low energy impulse. After the back-up impulse is applied, the NC template may be generated and stored (operation 714).

FIG. 8A illustrates generation of each of the H+V and NC templates based on a single set of response characteristics obtained after a respective impulse is applied by the stimulation device 10. In other implementations, the H+V and NC templates may be generated by collecting multiple sets of response characteristics following multiple applications of high and/or low energy impulses, respectively. The collected sets of response characteristics may then be combined to generate each of the H+V and NC templates. Accordingly, the values or ranges of values for particular response characteristics stored within the H+V and NC templates may be based on one or more measurements and may include, without limitation, averages, ranges, and similar statistical values derived from multiple response characteristic measurements.

Following generation and storage of the H+V and NC templates, the stimulation device 10 applies impulses having different stimulation voltages. The resulting responses for each impulse are then measured, analyzed, and classified based on the cardiac tissue captured as a result of each impulse. For example, in the implementation illustrated in FIG. 8A, initial impulse stimulation voltage ($V_{STIM}$) and impulse timing are each set (operations 716, 717).

The initial $V_{STIM}$ is generally set to a high starting voltage from which classification is to begin. In certain implementations, the initial voltage value may be, without limitation, one of the maximum output voltage of the stimulation device 10, the voltage previously used to generate the H+V template in operations 702-706, and a voltage that is a predetermined step below the voltage used to generate the H+V template.

The initial impulse timing may vary based on the configuration and mode of the pacemaker or defibrillator device used. For example, in the presence of an atrial lead and ventricular tracking (e.g., "DDD" pacing), the His capture threshold test may be run with an AV delay short enough to prevent competition with intrinsic conduction. This can be achieved, for example, by first lengthening the atrial sensing-to-ventricular pacing delay (for example, to 200 ms) to determine the intrinsic conduction duration. If there is an inhibition of ventricular pacing then the atrial sensing-to-ventricular pacing delay may be shortened (for example to 100 ms) and tested again. If ventricular sensing occurs, then the atrial sensing-to-ventricular pacing delay may be further shortened, for example, to 50 ms. A similar procedure can be followed for DDD devices in which atrial pacing is implemented.

If the implemented device does not include atrial lead or is otherwise programmed to operate in a single chamber mode, such as a "VVI" mode, the capture test should generally be performed at a rate that is faster than the underlying heart rate. This may be done by setting the base rate to a programmed base rate plus a predetermined rate increase (e.g., 10 ppm) for a predetermined time period (e.g., 30 seconds) and measuring the underlying rate. For example, measuring the underlying rate may be performed by calculating R-R intervals for heart beats measured during the predetermined time period. If there is no inhibition of ventricular pacing due to ventricular sensing, then the base rate may be set at the programmed base rate plus the predetermined rate increase. In alternative implementations, each of an average R-R interval and standard deviation may be determined over a predetermined time period and the base rate may be calculated based on a heart rate calculated from the R-R interval plus a factor based on the standard deviation. For example, in certain implementations, a heart rate may be calculated using the formula $HR_{AV}=60000/(R\text{-}R\ \text{interval})$, where the R-R interval is measured in milliseconds. The ventricular pacing rate may then be set to $HR_{AV}$+ 3*standard deviation (ppm). In certain implementations, the process of determining the base rate may be repeated to eliminate spurious results caused by fusion.

After establishing the initial impulse timing and $V_{STIM}$ settings, the stimulation device 10 then initiates the capture test by applying an impulse (operation 718) and measuring the resulting response characteristics (operation 720).

Referring to FIG. 8B, the impulse is then classified by analyzing the response characteristics measured during operation 720. In general, the process of classifying the response characteristics includes comparing the response characteristics to values or ranges of values to determine whether the response characteristics indicate capture of one or more of the His bundle and the right ventricle. For example, in certain implementations, the response characteristics are compared to templates stored within the stimulation device 10, such as the H+V and NC templates generated during operations 706 and 714, respectively. In instances when the template includes a range of values, determining whether a particular measured response characteristic indicates capture of certain cardiac tissue generally includes determining whether the measured response characteristic falls within the range of values. In contrast, when the template includes a single value, determining whether the measure response characteristic indicates capture may include determining whether the measured response characteristic falls within a certain tolerance of the stored value. For example, a match may be considered to occur when the measured response characteristic is within one or more of an absolute tolerance, a percentage-based tolerance, and a particular number of standard deviations (if the stored value was obtained from multiple measurements).

As shown in FIG. 8B, the response characteristics may first be compared to the H+V template (operation 724) to determine whether the response characteristics correspond to non-selective capture of the His bundle (i.e., capture of both the His bundle and the right ventricle). If so, $V_{STIM}$ is classified as inducing non-selective capture ("H+V") (operation 726) and the classification is stored or otherwise recorded (operation 760), such as in a classification table maintained in the memory 94 of the stimulation device 10.

For purposes of this disclosure, a classification table refers to a table or similar data structure maintained within the memory 94 of the stimulation device 10. The classification table includes multiple classification table entries that include a stimulation voltage and data corresponding to the stimulation voltage. The data may include, without limitation, one or more of a classification assigned during the automatic threshold capture test for the particular stimulation voltage and response characteristics generated by application of the particular stimulation voltage. Entries within the classification table may further be based on particular combinations of stimulation voltages and pulse durations such that each entry within the classification table corresponds to a unique combination of impulse voltage and duration. For ease of searching and analysis, the classification table may be organized or indexed in an ascending or descending order based on voltage/power. As described further in the context of FIG. 9, the classification table may be accessed by the microcontroller 60 of the stimulation device 10 to determine and change control output settings of the stimulation device 10.

If the response characteristics do not correspond to the H+V template, they are then compared to the NC template (operation 728). If the response characteristics correspond to those of the NC template, $V_{STIM}$ is classified as resulting in non-capture ("NC") (operation 730) and the classification results are stored in the classification table (operation 760). In certain implementations, an additional check may be performed to determine whether $V_{STIM}$ resulted in non-capture (operation 762). If capture occurred, $V_{STIM}$ may be updated (operation 764) and the process of applying an impulse using the updated $V_{STIM}$ and classifying the resulting response may be repeated. In the implementation illustrated in FIGS. 8A-8B, for example, $V_{STIM}$ is decreased by a predetermined voltage change ($\Delta V$). $\Delta V$ may be any suitable increment by which the output of the stimulation device 10 may be changed. Using a higher value for $\Delta V$ generally leads to a faster capture threshold test as fewer voltage levels of the stimulation device 10 are required to be tested. In contrast, a more granular $\Delta V$ may be used to increase the precision of the capture threshold test and, as a result, more accurately determine the voltage levels at which capture of particular cardiac tissues occur or are lost.

If application of an impulse at a particular $V_{STIM}$ results in non-capture, a back-up impulse may be applied (operation 766). Also, because any subsequent lower voltages are also likely to result in non-capture, any remaining voltage levels yet to be tested that are below $V_{STIM}$ may automatically be classified as NC within the classification table (operation 768).

Referring back to FIG. 8B, in certain instances, the response characteristics may not correspond to values representative of either of the H+V template and the NC template. In such instances, the response characteristics may be further analyzed to determine whether they indicate the occurrence of selective HBP, in which only the His bundle is captured, or ventricular pacing, in which only the right ventricle is captured. To do so, the response characteristics may be compared to values or ranges of values, which may be stored as additional templates and, more specifically, as a selective HBP ("H") template and a ventricular pacing ("V") template. Accordingly, and as illustrated in FIG. 8B, a check may be performed to determine whether either of an H template or a V template has been generated (operation 732). If so, the response characteristics may be compared to the H or V template (operation 744) and, if a match exists, the current $V_{STIM}$ may be classified accordingly (operation 746). The classification may then be stored in the classification table (operation 760).

If an H or V template does not currently exist, the response characteristics may be analyzed to determine whether they correspond to either selective HBP or to ventricular pacing and an H or V template may be generated. To do so, the QRS duration and the evoked response delay of the response characteristics may be compared to those of the H+V template. If the QRS duration is longer than that of the H+V template but the evoked response delay is approximately equal to that of the H+V template, it is likely that the current response characteristics are indicative of ventricular capture. Alternatively, if the QRS duration is approximately equal to that of the H+V template and the evoked response delay is longer, it is likely that the response characteristics correspond to selective HBP. In FIG. 8B, this process is simplified by determining whether the evoked response delay exceeds that of the H+V template (H+V). Accordingly, based on the outcome of the comparison, either a ventricular capture (V) template or a selective HBP template (H) or may be generated based on the response characteristics (operations 736, 740) and the response characteristics may be classified accordingly (operations 738, 742). The resulting classification may then be stored in the classification table (operation 760).

Due various factors, which may include the physiology of the heart and the location of stimulating electrodes, the method 700 will typically generate only one of the H and the V template. More specifically, heart physiology generally dictates one of two capture sequences as impulse energy is reduced. In the first sequence, high energy impulses result in non-selective HBP in which both of the His bundle and right ventricle are captured. As impulse energy is reduced, selective HBP occurs resulting from capture of the His bundle only. As impulse energy is further reduced, neither the His bundle or the right ventricle is captured. In the second sequence, high energy impulses similarly result in non-selective HBP. However, as impulse energy is reduced, only the right ventricle is captured and, as impulse energy is further reduced, non-capture results. As a result, if the physiology of the patient's heart conforms to the first sequence, only an H template is likely to be generated and if the physiology of the patient's heart results in the second capture sequence, a V template will be generated.

A number of scenarios may occur where the response characteristics do not match any of the generated templates. Such situations may include what are referred to herein as fusion, pseudo-fusion, and hemi-capture. Fusion occurs when conduction resulting from the impulse delivered during operation 718 coincides with the intrinsic conduction of the patient's heart. In contrast, pseudo-fusion occurs when an ineffective impulse is delivered during the absolute refractory period. In each of fusion and pseudo-fusion, the response characteristics resulting specifically from the impulse cannot be readily distinguished from the intrinsic response of the heart. Finally, hemi-capture occurs when the impulse results in capture of only one of the right bundle fibers and the left bundle fibers of the His bundle, leading to incomplete electrical communication between the His bundle and the ventricles.

To discriminate between fusion, pseudo-fusion, and hemi-capture, the timing of the impulse may be varied (operation 752). More specifically, the delay between sensing electrical activity and delivering an impulse to the His bundle is varied from the timing implemented during operation 718. For example, in implementations including each of an atrial lead and a His bundle lead, the timing between sensing electrical activity of the atrium (e.g., by observing a P wave) and applying an impulse to the His bundle may be increased or decreased by a predetermined interval. The impulse is reapplied using the new timing (operation 754) and a new set of response characteristics are measured (operation 756). The process of classifying the new response characteristics then proceeds to determine whether the new timing has resolved the inability to classify the original response characteristics. Subsequent storage of a classification table entry in the classification table (during operation 760) may further include storing the modified timing.

In certain implementations, the new response characteristics obtained using the modified timing are compared with the response characteristics originally obtained during operation 720 to provide further information and, more specifically, to identify whether the inability to classify the original impulse was the result of fusion, pseudo-fusion, or hemi-capture. If the response characteristics obtained using the modified timing are consistent with the originally obtained response characteristics, hemi-capture is likely. More specifically, if the evoked response delays and/or QRS complex morphology are consistent, it is likely that electrical impulses are unable to properly proceed through one of the left and right His bundle fibers. Similarly, comparison of the new and original response characteristics may identify the occurrence of pseudo-fusion and/or fusion. For example, if the timing between atrial sensing and His bundle pacing is increased, and the resulting response characteristics indicate consistent QRS morphology but a reduced evoked response delay, pseudo-fusion likely occurred. In contrast, if QRS morphology differs between the modified and original timing, fusion likely occurred.

Data corresponding to the identification and detection of fusion, pseudo-fusion, and hemi-capture may be stored within the memory 94 of the stimulation device 10 for later retrieval and diagnostic analysis. For example, in certain implementations, the stimulation device 10 may generate and store a log in which data corresponding to fusion, pseudo-fusion, hemi-capture, and similar events is recorded. Such data may include, without limitation, a date/time stamp, the response characteristics corresponding to the event, the stimulation device settings that resulted in the event, and the stimulation device settings that circumvented the event.

If response characteristics obtained using modified impulse timing are still unable to be classified, the impulse timing may be further modified and another set of response characteristics may be obtained and analyzed to determine whether classification is possible. In certain implementations, the number of times that the impulse timing is modified may be limited such that after the limit is exceeded, the current $V_{STIM}$ is classified as resulting in non-capture. Also, to the extent the response characteristics measured during operation 756 indicate non-capture of a portion of the heart tissue, a back-up impulse may be delivered.

C. Initialization of Stimulation Device Settings

Figure 9:
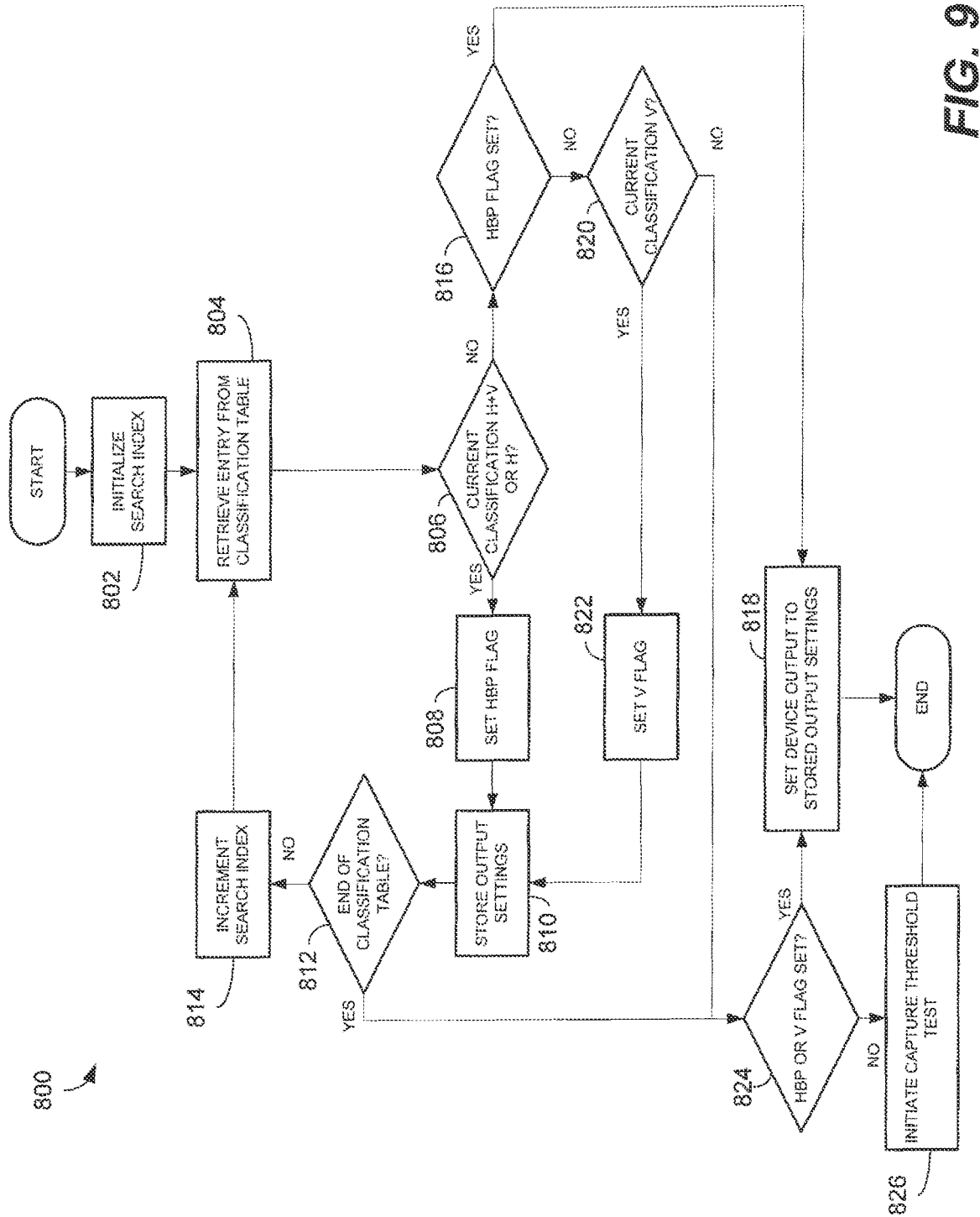
FIG. 9 is a flow chart illustrating a method for initializing a stimulation device, such as the stimulation device of FIG. 2.

FIG. 9 is a flow chart illustrating a method 800 of initializing output settings of a stimulation device, such as the stimulation device 10. In certain implementations, initialization of the stimulation device 10 includes identifying the lowest energy impulse capable of capturing the His bundle, regardless of whether capture of the His bundle is selective or non-selective. In the event that His bundle capture is not possible, initialization further includes identifying the lowest energy impulse capable of capturing the right ventricle.

During initialization, the stimulation device 10 and, more specifically, the microprocessor 60 of the stimulation device 10, determines and applies initial output settings. In certain implementations, the microprocessor 60 may search or otherwise analyze data stored in the memory 94 of the stimulation device 10 to determine the initial output settings. For example, the memory 94 may store a classification table including entries that form a list of possible output settings of the stimulation device 10 and corresponding classifications for the responses generated by applying an impulse according to the output settings. For purposes of the method 800, the output settings generally correspond to a His bundle electrode adapted to provide pacing of the His bundle, however, in configurations in which other pacing electrodes are implemented, additional output settings for pacing of other heart tissue may further be loaded by the stimulation device 10 during the initialization process.

The method 800 assumes that a classification table has been created that includes an ordered list of output settings arranged by output energy and that each entry in the classification table is associated with an index. The method 800 further assumes that the classification table is arranged or indexed such that as the search index is incremented, the classification table entries that are retrieved and analyzed correspond to progressively lower output settings. Accordingly, the method 800 includes initializing a search index (operation 802) and retrieving an entry corresponding to the index from the classification table (operation 804).

The retrieved record is then analyzed to determine whether the entry corresponds to settings that were previously classified (such as during the threshold capture test illustrated in FIGS. 8A-8B) as evoking either non-selective (H+V) or selective (H) His bundle capture (operation 806). If the output settings of the current classification table entry resulted in His bundle capture, a flag (HBP flag) is set indicating that an HBP-suitable setting has been identified (operation 808) and the output settings are stored as potential output settings of the stimulation device 10 (operation 810). If the current index does not correspond to the end of the classification table (operation 812), the search index is incremented (operation 814) and the process of retrieving and analyzing the corresponding classification table entry is repeated. To the extent subsequent classification table entries are also classified as either H or H+V, the temporarily stored settings will continue to be updated to reflect the lowest power settings for which His bundle capture was identified.

If the current classification table entry is not classified as either H or H+V, a check is performed to determine whether the HBP flag has been set (operation 816). In other words, a check is performed to determine whether output settings are currently stored that result in capture of the His bundle. If the HBP flag is set, the stored settings are applied to the stimulation device 10 (operation 818) and the initialization process ends. In certain implementations, application of the stored settings to the stimulation device 10 includes setting the output setting of the stimulation device 10 to match the stored output settings. In other implementations, the output settings of the stimulation device 10 may correspond to the stored output settings augmented by a safety factor. The safety factor may include, without limitation, one or more of a quantity added to one or more of the stored output settings or a factor by which one or more of the stored output settings are multiplied.

If, on the other hand, the HBP flag has not been set, the implication is that no output settings were identified that resulted in His bundle capture. A check is then performed on the current classification table entry to determine whether it has been classified as resulting in ventricular capture (V) (operation 820). If so, a corresponding flag (V flag) is set (operation 822), the output settings corresponding to the current classification table entry are stored (operation 810), and the search index is incremented (operation 814). To the extent any subsequent classification table entries are also classified as V, the stored output settings will be updated such that the stored output settings reflect the lowest output settings capable of ventricular capture.

When the end of the classification table is reached (as determined by operation 812) or the current classification table entry is not classified as any of H, H+V, or V (as determined by operation 820), a check is performed to determine whether either of the HBP or V flags have been set (operation 824), thereby checking whether output settings have been stored. If so, the output settings of the stimulation device 10 (operation 818) are set to the stored output settings and the initialization process ends.

If neither of the HBP or V flag has been set, then the initialization process failed to identify any settings capable of capturing either the His bundle or ventricle and remedial measures may be initiated. For example, in the method 800, a capture threshold test, such as the capture threshold test illustrated in FIGS. 8A-8B, may be initiated to generate an updated classification table. In certain implementations, capture threshold testing may also be initiated upon determining that the classification table does not include any entries classified as resulting in His bundle capture (i.e., H+V or H).

D. Post-Initialization Operation of Stimulation Devices

Figure 10:
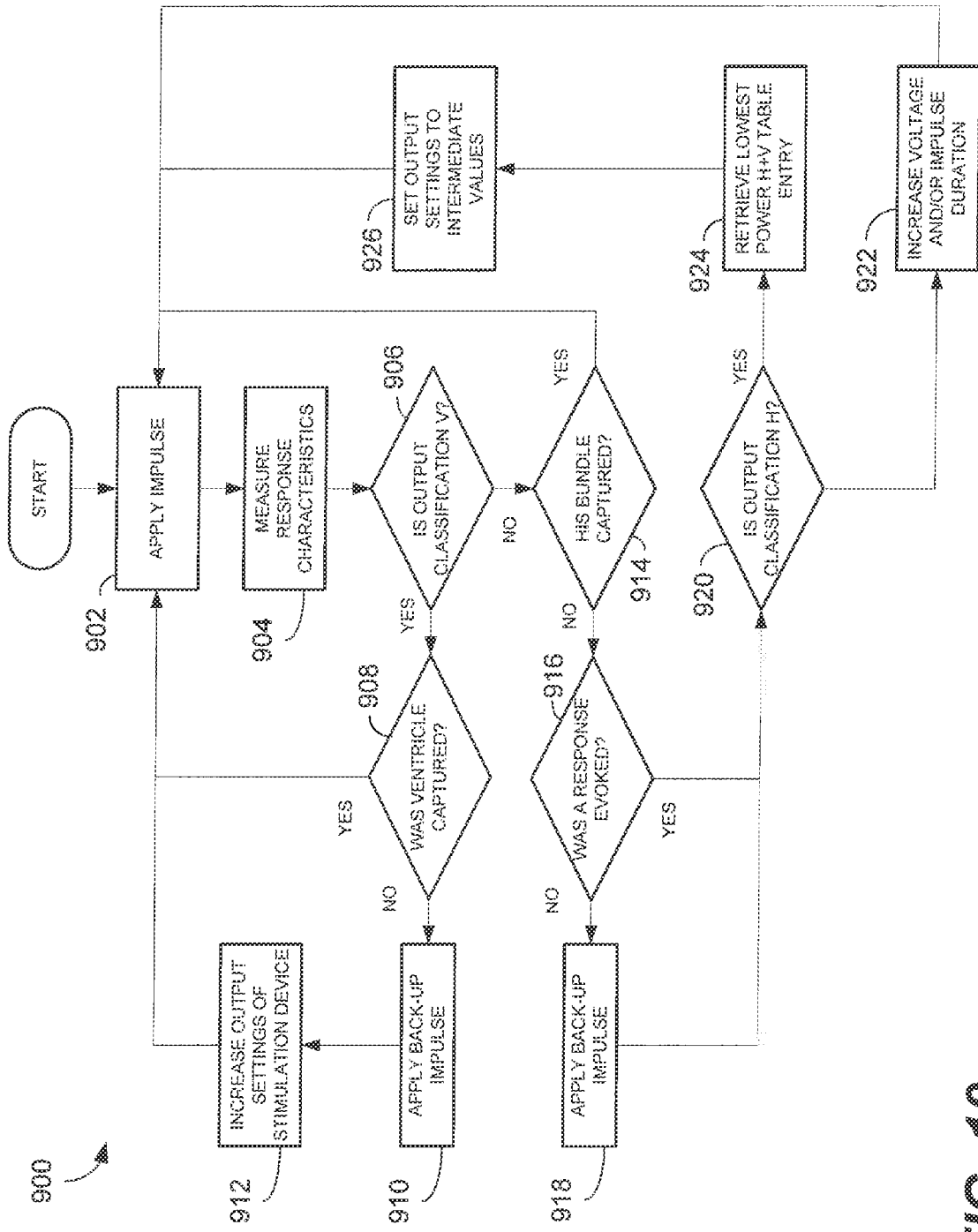
FIG. 10 is a flow chart illustrating a method for operating a stimulation device, such as the stimulation device of FIG. 2.

FIG. 10 illustrates a method 900 of operating a stimulation device 10 subsequent to the initialization process illustrated in FIG. 9. In general, operation of the stimulation device 10 includes applying an impulse based on the current output settings of the stimulation device 10, measuring response characteristics resulting from application of the impulse, and determining whether the response characteristics are consistent with the classification associated with the output settings of the stimulation device 10. To the extent the response characteristics are inconsistent with the classification, the output settings of the stimulation device 10 are modified for the subsequent impulse. The method 900 presumes that the output settings of the stimulation device 10 have been initialized. Initialization of the output settings may include executing an initialization process, such as that illustrated in FIG. 9, or may include loading previously stored output settings.

The method 900 includes applying an impulse (operation 902) according to the settings applied during initialization and measuring the corresponding response characteristics (operation 904). Following measurement of the response characteristics, a check is performed to determine whether the current output settings were previously classified as inducing ventricle-only capture (V) (operation 906). If so, a subsequent evaluation of the response characteristics is performed to determine whether the ventricle was capture (operation 908). Evaluation of the response characteristics may include comparison of the response characteristics to one or more templates including values or ranges of values indicative of ventricle-only capture. Such templates may, for example, be generated as part of a capture threshold test, such as the capture threshold test illustrated in FIGS. 8A-8B.

If the response characteristics are consistent with ventricle-only capture, the operational loop is reinitiated by applying a subsequent impulse using the existing output settings. If, on the other hand, the ventricle was not captured, a back-up impulse may be applied (operation 910) and the output settings of the stimulation device 10 may be increased (operation 912). Increasing the output settings of the stimulation device 10 may include, without limitation, increasing one or both of the output voltage and pulse duration settings of the stimulation device 10. Increasing an output setting may include, without limitation, one or more of increasing the output setting by a predetermined amount, multiplying the output setting by a predetermined factor, or modifying the output setting based on settings data stored within a classification table. In implementations in which the output settings are modified based on a classification table, such modification may include identifying the next highest output setting classified as resulting in ventricle-only capture and setting the output settings of the stimulation device 10 to the next highest output setting. Alternatively, the output settings of the stimulation device 10 may be set to an average or weighted average of the current and next highest output settings.

If the output settings of the stimulation device 10 are not classified as ventricle-only capture, a subsequent check may be performed to determine if the impulse resulted in capture of the His bundle (operation 914). If the His bundle was captured, the operational loop may be reinitiated. Alternatively, a check may be conducted to determine whether the impulse evoked a response (operation 916), such as a QRS complex, by analyzing the response characteristics. In the event the impulse did not produce a response, a back-up impulse may be applied to ensure a heartbeat (operation 918).

Whether a response was evoked by the original impulse or the back-up impulse, the original impulse is then modified in an attempt to adjust the output settings to result in His bundle capture. Generally, modifying the output settings involves increasing at least one of the output voltage and impulse duration, thereby increasing the overall energy of the impulse. As previously discussed in the context of ventricle-only capture, modification of the output settings of the stimulation device 10 may include, without limitation, one or more of increasing an output setting of the stimulation device 10 by a predetermined amount, multiplying the output setting by a predetermined factor, or modifying the output setting based on settings data stored within a classification table.

In certain implementations, the type of modification applied to the output settings may vary based on the classification assigned to the original output settings of the stimulation device 10. For example, in the method 900 a check is performed to determine whether the initial output settings were classified as resulting in selective His bundle capture (H) (operation 920). If not, the method 900 assumes the original classification corresponded to non-selective His bundle capture (H+V) and one of the voltage and impulse duration is increased by a predetermined amount (operation 922). If, on the other hand, the original output settings were classified as H, a more complex modification is undertaken. Specifically, the lowest power entry in the classification table resulting in non-selective His bundle capture is identified and retrieved (operation 924). The output settings of the stimulation device 10 are then changed to an intermediate value between the current output settings and those corresponding to the lowest power H+V table entry (operation 926).

After modification of the output of the stimulation device 10, the process of applying an impulse based on the current settings of the stimulation device 10, measuring corresponding response characteristics, and analyzing the response characteristics to determine if they are consistent with the output setting classification are repeated. In certain implementations, failure to capture the His bundle may automatically trigger initiation of a capture threshold test, such as the capture threshold test illustrated in FIGS. 8A-8B.

The methods illustrated in FIGS. 8A-10 are example methods in which sensing and stimulation are applied primarily to the His bundle and the right ventricle. In other implementations in accordance with this disclosure, other heart tissue may be sensed and stimulated instead of or in addition to the right ventricle. Such heart tissue may include, without limitation, one or more of the right atrium, the left atrium, and the left ventricle. For example and with reference to FIGS. 8A-8B, in certain implementations, the "V" template may correspond to a response of any of the left ventricle, the right atrium, and the left atrium instead of the right ventricle. Alternatively, in addition to the "V" template corresponding to a response of the right ventricle, additional templates may be generated for one or more of the left ventricle, the right atrium, and the left atrium. In either case, the templates corresponding to the left ventricle, the right atrium, and the left atrium may be used instead of or in conjunction with a template corresponding to the right ventricle for purposes of classifying impulses (for example, as illustrated in FIGS. 8A-8B) and dynamically controlling an implantable cardiac stimulating device (for example, as illustrated in FIG. 10).

Implantable cardiac stimulating devices in accordance with this disclosure may also store data related to their operation and may make such data available for retrieval and analysis. For example, and referring to the stimulation device 10 depicted in FIGS. 2 and 4, data may be collected and stored by in the memory 94 and made available to one or more external devices, such as the external device 102, using the telemetry circuit 100. In certain implementations, data made available from the stimulation device 10 may include, without limitation, any templates generated and/or stored within the stimulation device for classifying impulse responses, classification tables used to initialize settings of the stimulation device 10, and one or more logs used to record one or both of device activity and cardiac activity. Such data may be recorded over time to facilitate identifying trends that may correspond to changes in the stimulation device 10 or components thereof or the cardiac tissue to which the stimulation device 10 is coupled. For example, such trend data may include a summary diagnostic that may include a count or percentage of selective and non-selective His bundle pacing events over a period of time. As another example, such data may include measurements of the capture threshold over time, which may be used to identify improvement or degeneration of heart tissue based on whether the capture threshold is decreasing or increasing over time, respectively.

In implementations in accordance with this disclosure, the stimulation device 10 captures and analyzes electrical activity of the heart for various purposes. For example, in the method 700 of FIGS. 8A and 8B, response characteristics produced by applying an impulse to the heart are measured during various operations (for example, each of operations 704, 710, and 720). One characteristic that may be determined and used to evaluate whether His bundle capture has occurred and whether the capture is selective of non-selective is the duration of the QRS complex produced subsequent to the application of an impulse by the stimulation device 10. Accordingly, stimulation devices in accordance with this disclosure may be able to determine the duration of a QRS complex using various methods.

FIG. 11 is a flow chart describing an example method 1100 for determining QRS complex duration. Generally, the method 1100 involves identifying each of a start time and end time of the QRS complex and then determining the length of the interval between the start and end times. To do so, the method 1100 includes capturing electrical data (operation 1102), the electrical data corresponding to a cardiac response, such as a QRS complex, following application of an electrical impulse from a stimulation device. For example, the stimulation device may be configured to sample signals from sensing electrodes for a predetermined time period (e.g., 300 ms) following application of an impulse by the stimulation device and to store the sampled data. An example of such collected data is illustrated in FIG. 12, which depicts a graph 1200 including millivolt readings over time corresponding to a QRS complex following application of an electrical impulse to cardiac tissue.

After receiving the electrical data, the data may be processed and analyzed to determine the duration of the QRS complex. In the method 1100, for example, the absolute value of the first derivative of the electrical data is taken (operation 1104) such that an absolute rate of change of the electrical readings may be determined. The graph of FIG. 13 is a graph 1300 of the absolute first derivative of the electrical data of FIG. 12 and, as a result, depicts the absolute rate of change of the electrical activity (in millivolts (mV)/ms) over time.

The duration of the QRS complex may be determined from the absolute first derivative data in various ways. For example, in certain implementations, the maximum value of the absolute first derivative is identified (operation 1106). In the example data of FIGS. 12 and 13, the maximum absolute first derivative is 0.17 mV/ms and occurs at approximately 90 ms and is indicated by an "X" 1302. Next, a threshold value may be calculated based on the maximum value (operation 1108). The threshold value is generally selected to distinguish between possible noise or similar transients in the electrical signal and the actual electrical response of the cardiac tissue to the impulse and, as a result, may vary from application to application. In the current example, however, the threshold value is calculated as 5% of the maximum absolute first derivative, or approximately 0.0085 mV/ms, which is indicated in the graph 1300 by a threshold line 1304.

After establishing the threshold, the start time of the QRS complex is determined (operation 1110). In the current example, the absolute first derivative values are compared to the threshold beginning at the time the impulse was applied (t=Oms). The start time of the QRS complex is then identified as the time at which the absolute first derivative value first crosses the threshold 1304. In the example illustrated in FIG. 13, this occurs at approximately 50 ms and is indicated by a first dashed line 1306. The end time of the QRS complex may then be determined in a similar process (operation 1112). More specifically, the absolute first derivative values are compared to the threshold beginning at the end of the sampled data (i.e., t=250 ms). The end time of the QRS complex is then identified as the time at which the absolute first derivative value of the electrical signal crosses the threshold 1304, which is indicated in the graph 1300 with a second dashed line 1308. Referring again to the example in FIG. 13, the QRS complex end time occurs at approximately t=127 ms. The QRS duration may then be calculated (operation 1114), for example, by determining the difference between the QRS complex start time and the QRS complex end time and which in the example is approximately 77 ms. The calculated QRS complex duration may then be used to perform various evaluations and analyses as previously described herein including, but not limited to, the creation of templates and classification of impulse responses.

E. Classification of his Bundle Capture

His bundle pacing (HBP) has been shown to provide physiologically optimal ventricular stimulation, to promote atrioventricular and interventricular synchrony through intrinsic conduction pathways, and to eliminate the negative effects of long-term RV apical pacing. However, consistent and "selective" His bundle capture (i.e., capture of the His bundle alone, without also capturing the surrounding myocardium) is often difficult to maintain. Consequently, RV apical leads are often implanted for back-up pacing in case the His bundle lead falls to capture the His bundle. As a result, back-up RV pacing may automatically occur after a programmed delay in the event of non-capture of the His bundle.

His bundle pacing is unique in that an intermediate loss-of-capture scenario may exist in which an impulse delivered to the His bundle may not result in capture of the His bundle but may nevertheless capture local neighboring myocardial tissue. Such circumstances may be the result of, among other things, microscopic dislodgement of the His bundle pacing lead tip, tissue fibrosis that alters the lead tip-His tissue interface and capture threshold, or insufficient pacing impulse amplitude and/or duration. In such scenarios, additional capture verification methods must be employed. Thus, the ability to provide real-time, closed-loop, device-based feedback to verify selective His bundle capture out-of-clinic is important and has yet to be addressed. In the case of cardiac resynchronization therapy (CRT), in particular, achieving reliable and consistent selective His bundle capture generally results in an optimal QRS morphology and QRS duration with unique His-RV and His-LV timing.

In light of the foregoing, implementations of the present disclosure include methods to verify successful, selective His bundle capture in real-time. Such methods may be implemented using dual-chamber, CRT, or other stimulation devices which are generally equipped with electrodes to provide the required signal measurements on a beat-by-beat basis. Specifically, QRS morphology can be assessed using, among other things, far-field RV-coil-to-can EGMs; QRS duration can be estimated from such far-field EGMs; and His-RV and His-LV delays can be measured via sensing in the respective leads. As described herein, combinations of one or more of these metrics can be used as criteria to verify selective His bundle capture.

In certain implementations, one or more templates are established and stored within the stimulation device. For example, such a template may be generated in-clinic during initial testing of the stimulation device following implantation. Templates may also be generated as part of a threshold test, such as that illustrated in FIGS. 8A-8B and previously described in this disclosure. The one or more templates generally include a template for selective His bundle capture. Accordingly, a response of the heart to His bundle stimulation subsequent to the generation and storage of the templates may be collected and compared to the stored templates to classify the response and/or to verify the occurrence of selective His bundle capture. When loss of selective capture is detected, the stimulation device may automatically adjust settings, such as timing or pacing impulse parameters, until selective HBP capture is regained.

In light of the foregoing, this disclosure provides a closed-loop, device-based method to verify selective His bundle capture and to adjust the pacing timing, pulse amplitude, pulse-width, or other stimulation device settings as needed. In certain implementations, the stimulation device may be configured to measure responses to impulses applied to the His bundle by, among other approaches, one or more of QRS morphology based on the far-field EGM (e.g., RV coil-to-housing (or "can"), RA ring-to-can, or His ring-to-can EGMs); QRS duration estimates from the far-field EGM; or a sensed interval between pacing of the His bundle and depolarization of one or more chambers of the heart (e.g., the ventricles). In implementations in which QRS morphology is used to identify selective His bundle pacing, the far-field EGM may be based on, among other things, a RV lead coil-to-can measurement, a RA ring electrode-to-can measurement, or a His lead ring-to-can measurement.

In one implementation of the present disclosure, templates and/or corresponding values for one or more of QRS morphology, QRS duration, or ventricle sensing intervals may be established that represent one or more of intrinsic His-Purkinje conduction, selective His bundle capture, non-selective His bundle capture (i.e., capture of the His bundle and local myocardium), myocardium-only capture, and complete loss-of-capture (i.e., loss of capture for both the His bundle and the local myocardium). For each pacing impulse provided to the His bundle, the stimulation device may compare any combination of the aforementioned metrics to each of the templates within the stimulation device. Each beat may then be classified based on the comparison. If a particular response (e.g. selective His capture) is not achieved, the stimulation device may also adjust its settings accordingly such that subsequent pacing impulses provided to the His bundle are more likely to produce the desired response.

For example, suppose successful selective HBP is achieved during testing implantation of the stimulation device and results in an EGM-based QRS duration of 120 ms. When the pulse amplitude is slightly reduced during such testing, myocardium-only capture may result and the QRS duration may be increased to 140 ms. Based on these results, respective templates and/or metrics for selective and myocardium-only capture may be generated and stored in the stimulation device for use in analyzing the response to subsequent pacing impulses delivered to the His bundle. For example, the stimulation device may calculate EGM-based QRS duration for heart beats and compare the calculated QRS duration to the stored metrics/template.

Over time, fibrosis at the HBP lead tip, or other physiological changes may compromise the lead-His bundle interface. As a result, device settings and impulse parameters that previously resulted in selective His bundle capture may now only capture the myocardium surrounding the His bundle. By comparing the EGM-based QRS duration to the templates or values obtained and stored during earlier testing, the stimulation device may identify the loss of His bundle capture and may classify the resulting responses as indicating myocardium-only capture as opposed to selective His bundle capture. In certain implementations, after a predetermined number of responses indicate myocardium-only capture, the closed-loop feedback mechanism implemented in the stimulation device may automatically reprogram its pacing parameters, gradually adjusting the pulse width, pulse amplitude, or other pacing parameter until selective His bundle capture is achieved.

Although the foregoing example relied on an EGM-based QRS duration, other response metrics may be used to classify responses to His bundle pacing. For example, a QRS morphology template and/or His-RV/His-LV interval templates or similar metrics may be used to identify loss of selective His bundle capture. For example, QRS morphology during successful, selective His pacing may generally be narrower and potentially include fewer biphasic inflections or "bumps" in the waveform as compared to myocardium-only capture events. Similarly, the His-RV/His-LV intervals would generally be much shorter during selective His pacing as compared to responses involving myocardium-only capture.

If adjustments to impulse width, impulse amplitude, or other pacing parameters are not successful in re-establishing selective His bundle capture, a clinician may be notified via a notification system to adjust the HBP lead position, to implant a back-up RV lead if one does not already exist, or to otherwise intervene. In another example, the stimulation device may automatically adjustment atrial sensing-to-His pacing delays (when an atrial lead is implemented) or the His pacing rate (when no atrial lead is used) to ensure that His pacing does not result in fusion or pseudo-fusion. In yet another example, permanent HBP may be used to overcome left bundle branch block (LBBB). For example, by tracking EGM morphology and His-LV timing, LBBB may be identified and, if present, the pacing parameters of the stimulation device may be modified accordingly to overcome LBBB.

In one pre-clinical canine study, HBP was successfully provided using prototype His pacing leads and stimulation devices in accordance with the present disclosure and pacing amplitudes were adjusted to achieve various HBP scenarios, namely non-selective His capture and intrinsic conduction. As expected in a healthy canine heart, intrinsic beats exhibited narrower ECG QRS waveforms, i.e., had a shorter QRS duration, as compared to beats induced by HBP. These narrower QRS waveforms were also identified by the automated EGM-based QRS duration calculations executed by a stimulation as the QRS duration dropped from 59 to 51 ms. During each pacing scenario, the EGM-based QRS durations remained relatively stable and the reduction in QRS duration occurred at the first beat following the drop in pulse amplitude from 2.5 to 0.0 V.

During the study, reduction of the pulse amplitude to 2.0V resulted in myocardium-only capture, i.e., the His bundle was no longer captured. With the reduced pulse amplitude, the QRS duration noticeably increased. The change in QRS duration was identified by the automated EGM-based QRS duration calculations, which indicated an increase from 61 to 74 ms at the first beat following the 0.5 V drop in pulse amplitude. In this example, the pulse amplitude was intentionally dropped to capture various HBP scenarios. However, a similar situation could arise in the days following a HBP lead implant, when tissue inflammation or fibrosis could result in an elevation in the capture threshold. As a result of such physiological changes, His capture (non-selective in this example) could become myocardium-only capture.

The foregoing examples illustrate only some of the metrics outlined above (QRS duration estimates and EGM morphologies) and reflect only a subset of the HBP scenarios that may be achieved (i.e., intrinsic His-Purkinje conduction, non-selective His capture, selective His capture myocardium-only capture, and non-capture retained). However, the foregoing method can be easily applied using each of the identified metrics and corresponding templates to identify each possible His bundle pacing scenario.

Figure 14:
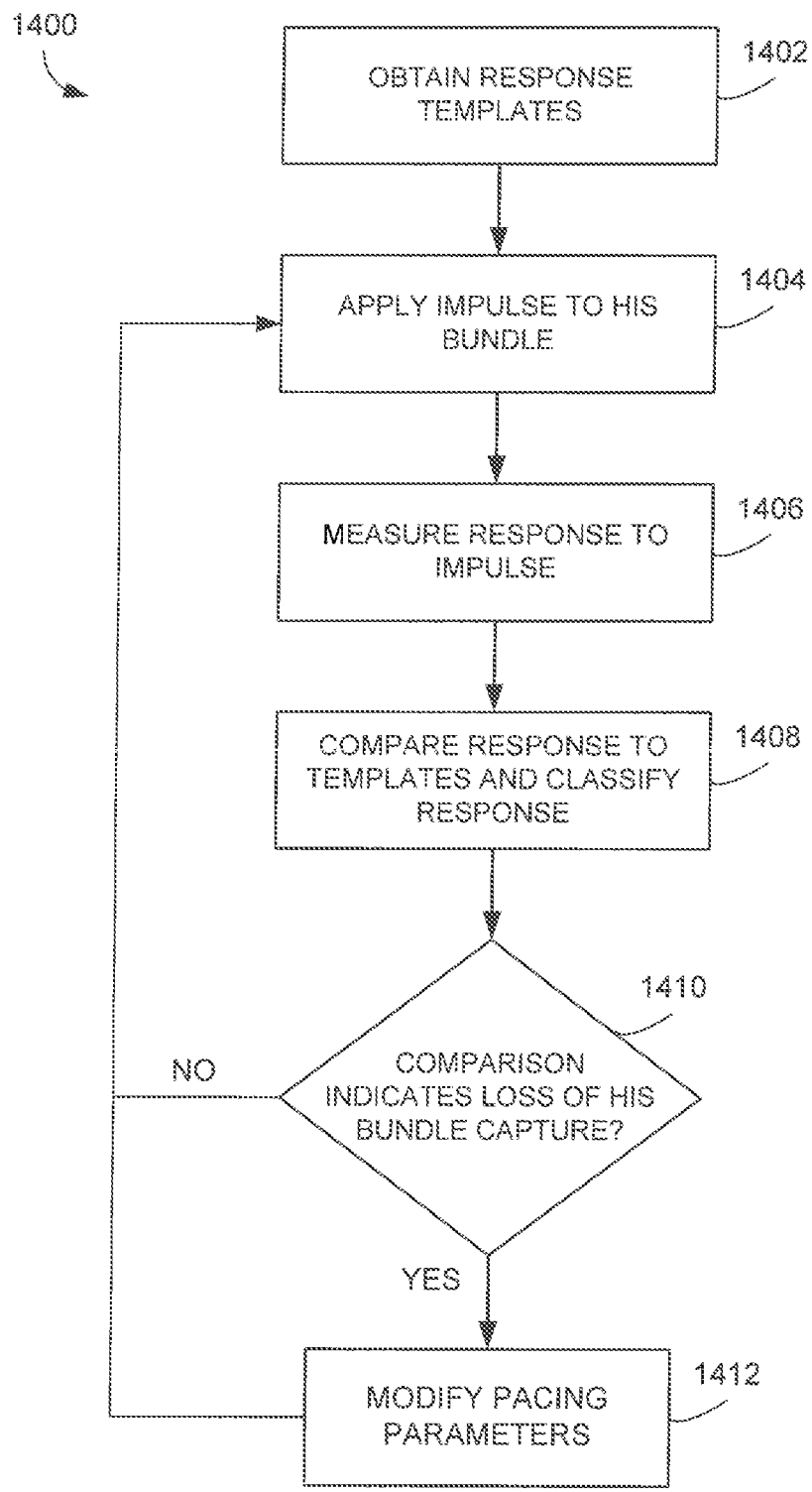
FIG. 14 is a flow chart illustrating an method of classifying His bundle capture.

FIG. 14 illustrates an example method 1400 of classifying His bundle capture in accordance with the present disclosure. The method 1400 begins with obtaining, at a stimulation device, a set of response templates (operation 1402). As previously discussed, the response templates may include example QRS responses or metrics associated therewith corresponding to different cardiac events. For example, the templates may include templates corresponding to, among other things, selective His bundle capture, non-selective His bundle capture, myocardium-only capture, non-capture, and intrinsic activation. In certain implementations, the templates may be programmed into the stimulation device after implantation, such as during a clinical testing regimen. Generation of the templates may also be conducted as part of a threshold test, such as the threshold test illustrated in FIGS. 8A and 8B of the present disclosure. Once obtained, the templates may be stored within a memory of the stimulation device.

At operation 1404 an impulse is applied to the His bundle using a lead of the stimulation device. A response to the impulse is then measured at operation 1406. In certain implementations, measurement of the response may include measuring electrical activity using electrodes of the stimulation device implanted within the heart. For example, a response to a given impulse may be measured by a far-field EGM based on, among other things, a RV lead coil-to-can measurement, a RA ring electrode-to-can measurement, or a His lead ring-to-can measurement. Additional measurements may also be collected from various electrodes of leads implanted within the heart and electrically coupled to the stimulation device. For example, one or more electrodes of leads implanted within the RV and/or LV may be used to measure corresponding electrical activity in those chambers of the heart.

At operation 1408, the stimulation device compares the response with one or more of the stored templates in order to classify the response. For example, in certain implementations, the measured response may provide a QRS waveform whose morphology may be compared to QRS waveforms of the various stored templates. In addition to QRS morphology, other characteristics of the measured response may also be considered including, without limitation, one or more of QRS delay, QRS duration, QRS onset delay, and the like. By comparing the response to the stored templates, the response may be classified based on the template to which the response most closely conforms.

At operation 1410, the stimulation device determines whether the prior comparison indicates a loss of His bundle capture. For example, in certain implementations, the stimulation device may identify a loss of His bundle capture if a first response is classified as indicating selective or non-selective His bundle capture while a subsequent response indicates myocardium-only capture or non-capture. In certain implementations, the stimulation device may identify a loss of His bundle capture when a predetermined number of consecutively measured responses indicate myocardium-only capture or non-capture.

If His bundle capture has not been lost, the stimulation device may initiate delivery of a subsequent His bundle pacing impulse (operation 1404). If, on the other hand, a loss of His bundle pacing is identified, the stimulation device may automatically adjust one or more pacing parameters (operation 412). For example, among other things, the stimulation device may increase one or both of the amplitude and the duration of impulses provided by the stimulation device, thereby increasing the overall energy of impulses delivered to the His bundle. In certain implementations, modifying the impulse settings may also include performing a threshold or similar test to verify that the new impulse settings will result in recapturing the His bundle. One example of such a test is described in the context of FIGS. 8A-8B above. Once the pacing parameters have been modified, the process of applying a subsequent impulse to the His bundle (operation 1404) and measuring and classifying the corresponding response (operations 1406 and 1408) may be performed again using the updated pacing parameters.

F. Tracking and Optimization of Ventricular Pacing

If intact, the His-Purkinje conduction system allows electrical stimulation to rapidly propagate into both right and left ventricles, ensuring synchronized ventricular contraction.

Early studies have demonstrated that distal His bundle pacing (HBP) may be used to normalize bundle branch block and QRS morphology. Accordingly, permanent HBP may provide physiological activation, reduce the ventricular dyssynchrony associated with separately pacing LV and RV, and preserve ventricular function.

Although HBP is promising, the potential impact of progressive conduction tissue disease and other physiological changes on capture, electrical synchrony, and long-term effects of HPB are not well known. Nevertheless, such diseases and changes can have a significant impact on the characteristics and timing of impulses required to capture the His bundle. For example, if pacing of the His bundle is not properly timed, progression in left bundle branch disease may lead to dyssynchrony during HBP.

Among other things, the present disclosure provides a method to evaluate His bundle capture and electrical conduction times (e.g., His-LV and His-RV) in patients with a cardiac resynchronization therapy (CRT) device or similar stimulation device. In general the systems and methods disclosed involve stimulation of the His bundle and measurement of one or more corresponding ventricular responses. The characteristics of such responses may be used to determine, among other things, tissue health, whether backup impulses should be directly provided to the ventricles, and whether settings of the stimulation device for providing HBP should be modified.

The methods disclosed herein generally include applying a stimulating impulse to the His bundle using an electrode of a stimulation device. Following application of the impulse, the stimulation device measures electrical conduction time between application of the impulse and depolarization of one or both of the ventricles. The stimulation device may further obtain an EGM or similar waveform corresponding to electrical activity of the heart in response to the impulse. The timing and waveform information gathered may then be used to assess tissue disease progression and to determine whether backup RV and/or LV pacing needs to be applied, among other things.

In one implementation of the current disclosure, the stimulation device may store one or more templates, metrics, or other values for evaluating the measured responses. For example, the stimulation device may store example EGM waveforms, QRS complexes, or values associated with waveforms or complexes corresponding to various capture/ activation scenarios (e.g., selective His bundle capture, non-selective His bundle capture, myocardium-only capture, non-capture, intrinsic conduction, etc.). The stimulation device may also store values corresponding to activation/ depolarization of various regions of the heart, such as a delay between pacing of the His bundle and depolarization of one or both of the LV and RV. In certain implementations the stimulation device may include one or more multi-polar leads, each of which includes multiple electrodes that may measure depolarization of different portions of a chamber of the heart within which the lead is implanted. In such implementations, the stimulation device may store delay values corresponding to each of the electrodes, a subset of the electrodes, or an average (or other combination) of some or all of the electrodes.

In certain implementations, the templates or other metrics associated with ventricular depolarization may be loaded into the memory of the stimulation device. For example, the templates and metrics may be identified and programmed into the stimulation device during in-clinic testing of the stimulation device following implantation. In other implementations, the stimulation device may be configured to automatically execute one or more routines for generating the templates and metrics. Such routines may, for example, be similar to the threshold test described above in the context of FIGS. 8A-8B.

During operation and as described below in more detail, the stimulation device is configured to pace the His bundle and to measure delays between application of pacing impulses and depolarization of the ventricles. The stimulation device may further record a resulting EGM or other waveform (or related metrics) associated with a response of the heart to the impulse. The delays may then be compared to the templates, values, etc. stored within the stimulation device. A further comparison of the EGM or other waveform to a stored template may also be conducted to determine whether the measured response corresponds to an ectopic beat. Based on the comparison of delays and whether or not the response corresponds to an ectopic beat, the stimulation device may apply backup impulses to one or both ventricles. In certain implementations, the stimulation device may also determine whether His bundle capture has been lost and, if so, to automatically initiate a threshold test or similar reconfiguration to modify the settings of the stimulation device in order to reestablish capture of the His bundle.

In certain implementations, the stimulation device may include logging and monitoring functionality. For example, the stimulation device may be configured to generate a log entry if and when an ectopic beat is detected. Such a log entry may include, among other things, a timestamp indicating when the ectopic beat occurred, one or more of the device settings, metrics associated with the corresponding measured response, and the like. In other implementations, other log entries corresponding to other activity and measurements of the stimulation device may be logged. Log entries may be retrieved during subsequent interrogation of the stimulation device and analyzed by a physician to identify any potential issues with operation of the stimulation device, physiological changes of the patient, or other circumstances that may require intervention (such as modification of the stimulation device settings or repositioning of a lead of the stimulation device).

Figure 15:
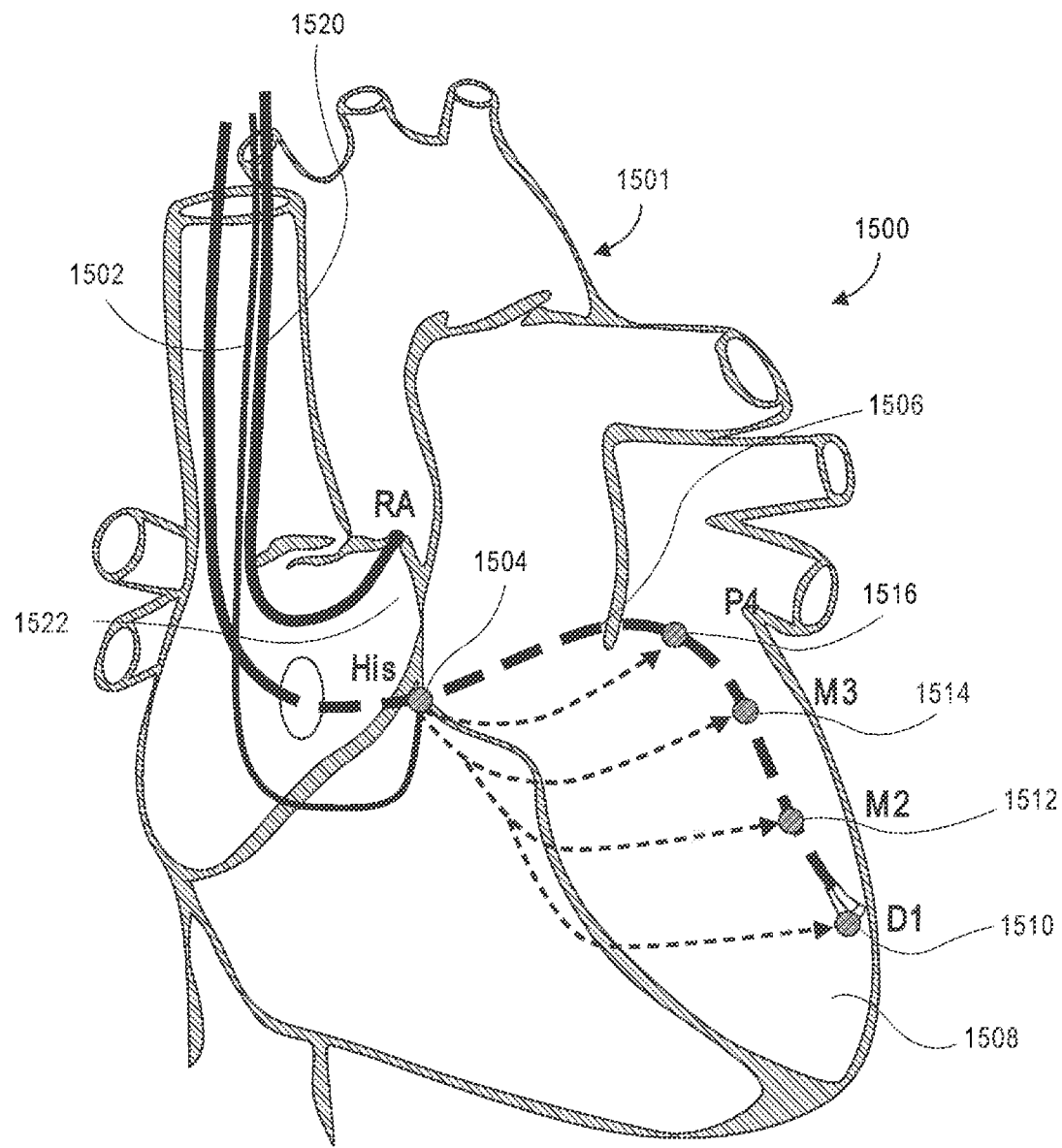
FIG. 15 is a schematic illustration of a stimulation system for providing pacing of the His bundle and left ventricle of a patient heart.

FIG. 15 is a schematic illustration of a stimulation system 1500 having a set of leads implanted within a patient heart 1501 according to one implementation of the present disclosure. The stimulation system 1500 includes each of a His bundle lead 1502 for pacing of the His bundle 1504 and a LV lead 1506 that extends into the LV 1508 for measuring electrical activity and providing pacing of the LV 1508. As illustrated, the LV lead 1506 includes four electrodes, indicated from most distal to most proximal as D1 1510, M2 1512, M3 1514, and P4 1516, disposed along its length. In general, each of the electrodes 1510-1516 is configured to measure electrical activity within respective areas of the patient heart 1501 and, at least in the case of D1 1510, to deliver pacing impulses to the LV 1508 as well. The stimulation system 1500 may further include an RA lead 1520 for pacing and/or monitoring electrical activity of the RA 1522.

Figure 16:
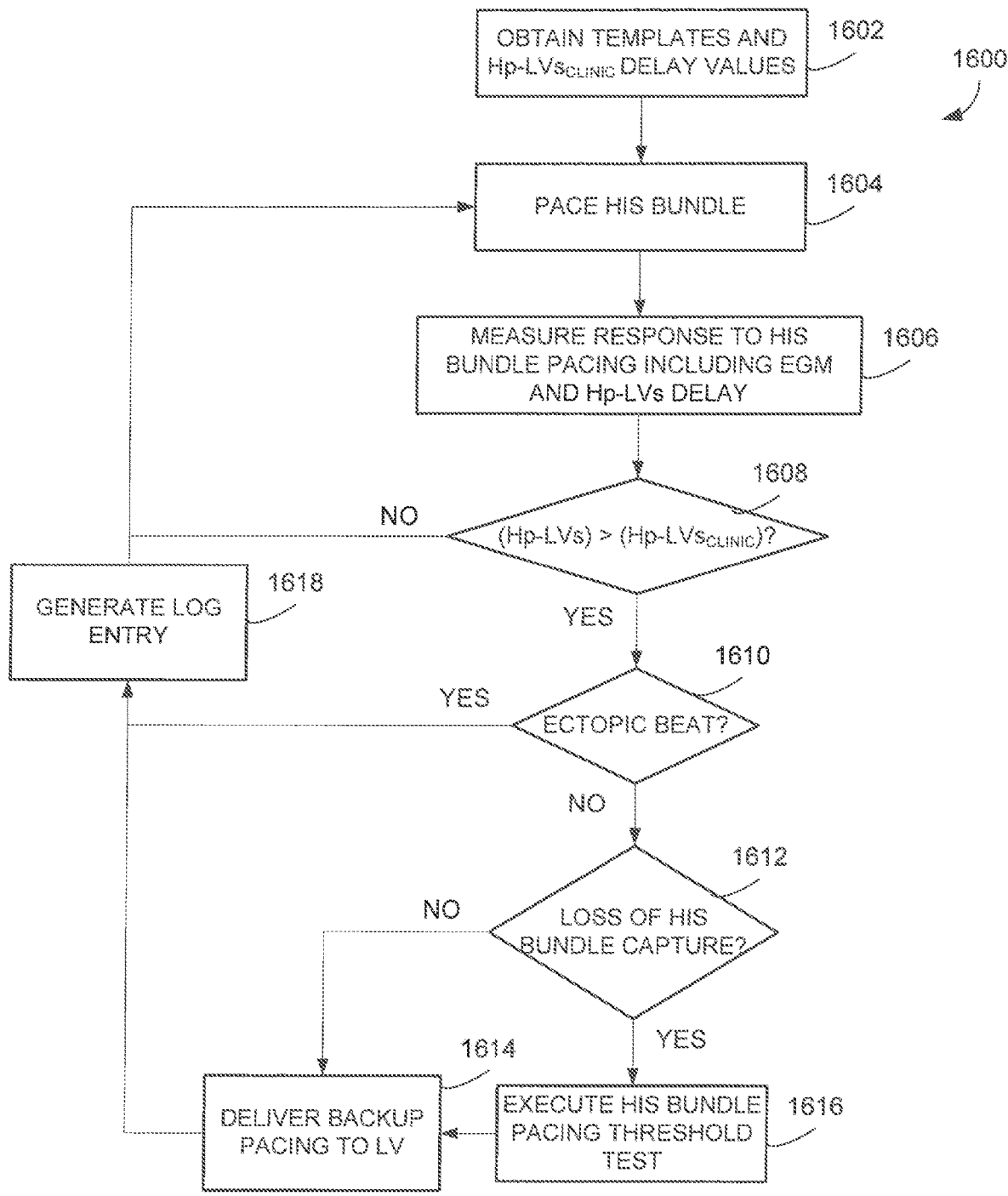
FIG. 16 is a flow chart illustrating a method for tracking and optimizing ventricular pacing delays that may be implemented using the stimulation system of FIG. 15.

Referring now to FIG. 16, a method 1600 for tracking and optimizing ventricular pacing delays is provided that may be implemented using stimulation systems, such as the stimulation system 1500 of FIG. 15. Although the following description makes reference to the stimulation system 1500 and its various components, it should be appreciated that the method 1600 may be implemented using other stimulation system arrangements.

At operation 1602 the stimulation system 1500 obtains and stores templates, values, and/or other metrics for use in analyzing measured responses to His bundle pacing impulses. In certain implementations, the stimulation system 1500 may store a set of templates corresponding to example EGM waveforms, QRS complexes, or values associated therewith, with each template representing a particular cardiac event. The templates may include templates corresponding to, among other things, selective His bundle capture, non-selective His bundle capture, myocardium-only capture, non-capture, and intrinsic activation. In certain implementations, the templates may be programmed into the stimulation device 1500 after implantation such as during post-implantation clinical testing regimen. Generation of the templates may also be conducted as part of a threshold test, such as the threshold test illustrated in FIGS. 8A and 8B of the present disclosure. Once obtained, the templates are stored within a memory of the stimulation system 1500.

For purposes of the current example, operation 1602 includes obtaining at least one value (Hp-LV$_{CLINIC}$) corresponding to the delay between pacing of the His bundle 1504 and depolarization of the LV 1508 as measured during clinical testing following implantation. As a result, Hp-LVs$_{CLINIC}$ provides a baseline for the delay between His bundle pacing and depolarization of the LV 1508 against which subsequently measured LV depolarization delays may be measured. In implementations including multipolar leads, values for Hp-LV$_{CLINIC}$ may be obtained for each electrode of the LV lead 1506. In the stimulation system 1500 of FIG. 15, for example, a set of Hp-Ls$_{CLINIC}$ values may be obtained, with at least one value corresponding to each of D1 1510, M2 1512, M3 1514, and P4 1516. In implementations in which a multipolar lead is used, Hp-LV$_{CLINIC}$ may also correspond to, among other things, a shortest or longest activation delay across all of the electrodes, a shortest or longest activation delay across a subset of electrodes, an average activation delay across all or a subset of the electrodes, or any other similar timing measurement.

At operations 1604 and 1606, a pacing impulse is applied to the His bundle 1504 is paced and a corresponding response to the pacing impulse is measured. As indicated in FIG. 16, the measured response may include an EGM measurement or similar waveform characterizing the electrical response of the heart to application of the His bundle pacing impulse in operation 1604. In certain implementations, the EGM measurement may be recorded by the stimulation device as a QRS waveform or as a set of values corresponding to particular characteristics (e.g., onset time, maximum amplitude, number and size of waveform peaks, etc.) of such a waveform. In addition to the EGM measurement, operation 1606 further includes measuring a delay between pacing of the His bundle 1504 and depolarization of the LV 1508 (Hp-LVs). In implementations in which a multipolar lead is used in the stimulation system 1500, Hp-LVs values for each electrode 1510-1518 of the LV lead 1506 may be measured in response to applying a pacing impulse to the His bundle 1504. Such a set of Hp-LVs values may be used to determine an activation order for the electrodes and, as a result, for various sections of the LV 1508. In such multipolar implementations, Hp-LVs may generally correspond to the particular metric embodied by Hp-Ls$_{CLINIC}$ (e.g., shortest activation time, longest activation time, average activation time, etc.).

At operation 1608, a comparison is made between the stored delay value for the LV 1508 (i.e., Hp-LVs$_{CLINIC}$) and the delay measured between pacing of the His bundle 1504 and subsequent depolarization of the LV 1508 (i.e., Hp-LVs). If Hp-LVs does not exceed or is approximately equal to Hp-LVs$_{CLINIC}$, it may be assumed that the conduction paths related to the LV 1508 are in substantially the same condition as represented by Hp-LVs$_{CLINIC}$. As a result, no interventions are taken by the stimulation system 1500 and the stimulation system 1500 may restart the process of applying a pacing impulse to the His bundle 1504 (operation 1604) and then measuring and assessing the resulting response (operations 1606 and 1608). If, on the other hand, Hp-LVs is found to exceed Hp-LV$_{CLINIC}$, such a change may be indicative of a change in the conduction paths of the heart, such as caused by a progressing cardiac disease or other physiological change in the patient's heart, that may warrant monitoring and/or intervention.

Although operation 1608 is illustrated in FIG. 16 as including a strict comparison between Hp-LVs and Hp-LVs$_{CLINIC}$, it should be appreciated that the comparison (and any similar comparison described herein) may instead involve comparison of Hp-LVs to a range of values corresponding to Hp-LVs$_{CLINIC}$. In one implementation, the comparison of operation 1608 may be between Hp-LVs and Hp-LVs$_{CLINIC}$ plus a margin or tolerance. For example, the stimulation device 1500 may continue normal operation (i.e., return to operation 1602) provided Hp-LVs does not exceed Hp-Ls$_{CLINIC}$ by more than a predetermined threshold (e.g., 5%, 10%, 15%, or any similar value). By doing so, the stimulation system 1500 may account for natural variability in the heart's response and avoid unnecessary intervention.

If Hp-LVs exceed Hp-LVs$_{CLINIC}$, the stimulation device 1500 may subsequently determine whether the measured response corresponds to an ectopic beat (operation 1610). Although various techniques may be implemented to determine the occurrence of an ectopic beat, in one implementation, the QRS waveform or corresponding metrics obtained in operation 1606 may be compared to one or more templates stored within the stimulation device 1500. For example, in one implementation a template may be stored that corresponds to an ectopic beat or the stimulation device 1500 may determine that if the response does not match one or more other stored templates, an ectopic beat has occurred. In yet another implementation in which a multipolar lead is used, an ectopic beat may be identified by a change in the activation order of the electrodes of the multipolar lead. If an ectopic beat is identified, the stimulation system 1500 may return to pacing of the His bundle 1504 (operation 1604) without further intervention. In certain implementations, a log entry of the ectopic beat may be stored within the memory of the stimulation system 1500, as indicated in operation 1618, which is described below in further detail.

If the response does not correspond to an ectopic beat, the stimulation system 1500 may perform an additional analysis to determine if capture of the His bundle has been lost (operation 1612). For example, in certain implementations, the QRS waveform or corresponding data obtained during operation 1606 may be compared to one or more of the stored templates to determine whether the measured response is indicative of His bundle capture (selective or non-selective) or another condition, such as myocardium-only capture or non-capture. If His bundle capture has not been lost, a backup pacing impulse may be delivered to the LV 1508, as indicated in operation 1614. If, on the other hand, His bundle capture has been lost, the stimulation device 1500 may initiate a His bundle pacing threshold test or similar testing operation to adjust settings of the stimulation device 1500 to recapture the His bundle (operation 1616). In general, such testing operations include applying His bundle pacing impulses having different amplitudes, durations, and/or timing and measuring the corresponding responses to determine which pacing parameters evoke certain types of responses. The stimulation device may then automatically configure itself based on the results of the test to achieve a desired response (e.g., selective His bundle pacing). One example of a threshold test that may be implemented by the stimulation device 1500 is described above in the context of FIGS. 8A-8B. Following execution of the threshold test in operation 1616, a backup pacing impulse may be provided to the LV 1508, as indicated in operation 1614.

In certain implementations, execution of the threshold test in operation 1616 may result in modification or replacement of at least some of the templates and/or metrics stored within the memory of the stimulation device 1500 for purposes. Accordingly, to the extent the stimulation device 1500 relies on metrics or templates stored within its memory to measure analyze measured responses to His bundle pacing, any subsequent analyses may be conducted using the updated or modified values.

Following or in conjunction with applying the backup pacing impulse at operation 1614, the stimulation system 1500 may generate and store a log entry (operation 1618). Log entries may also be generated and stored by the stimulation system 1500 in response to other conditions and events. For example, as previously discussed in operation 1618, the stimulation system 1500 may generate and store a log entry in response to detecting an ectopic beat, such as in operation 1610. Log entries may include, among other things, a date/time stamp, one or more metrics corresponding to a measured response, the settings of the stimulation system associated with a delivered impulse, a classification of a response (e.g., selective versus non-selective His bundle pacing), and the like. The log maintained by the stimulation system 1500 may be retrieved or provided to a physician or technician, such as by interrogating the log, such that the log entries may be analyzed or otherwise assessed for changes in the patient's condition, changes in the functioning of the stimulation system 1500, or other similar trends in the interaction between the patient and the stimulation system 1500.

Figure 17:
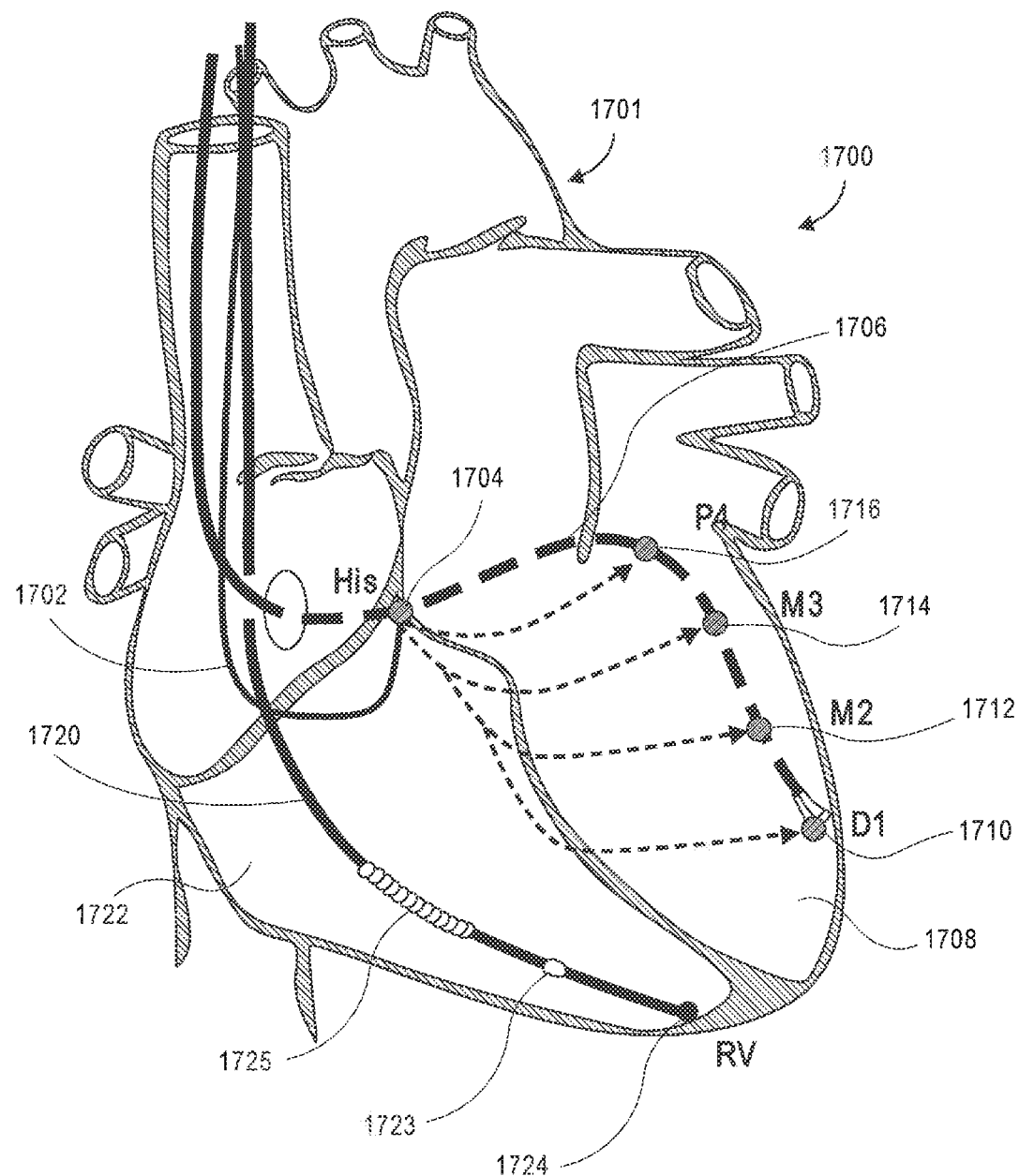
FIG. 17 is a schematic illustration of a stimulation system for providing pacing of the His bundle, left ventricle, and right ventricle of a patient heart.

FIG. 17 is a schematic illustration of a stimulation system 1700 having a set of leads implanted within a patient heart 1701 according to another implementation of the present disclosure. The stimulation system 1700 includes each of a His bundle lead 1702 for pacing of the His bundle 1704, a LV lead 1706 that extends into the LV 1708 for measuring electrical activity and providing pacing of the LV 1708, and a RV lead 1720 that extends into the RV 1722 for measuring electrical activity and providing pacing of the RV 1722. Although various leads may be used in implementations of the present disclosure, as illustrated, the LV lead 1706 includes four electrodes, indicated from most distal to most proximal as D1 1710, M2 1712, M3 1714, and P4 1716, disposed along its length. In contrast, the RV lead 1720 is illustrated as having a tip electrode 1724 and further including a shock coil 1725 and a ring electrode 1723. In general, each of the electrodes 1710-1716, 1723, and 1724 is configured to measure electrical activity within respective areas of the patient heart 1701 and, may be further adapted to pacing impulses to their respective implantation locations. Accordingly, in contrast to the stimulation system 1500 of FIG. 15, which provided sensing and pacing of the His bundle 1504 and the LV 1508 only, the stimulation system 1700 of FIG. 17 facilitates pacing and sensing of each of the His bundle 1704, the RV 1722, and the LV 1708.

Figure 18:
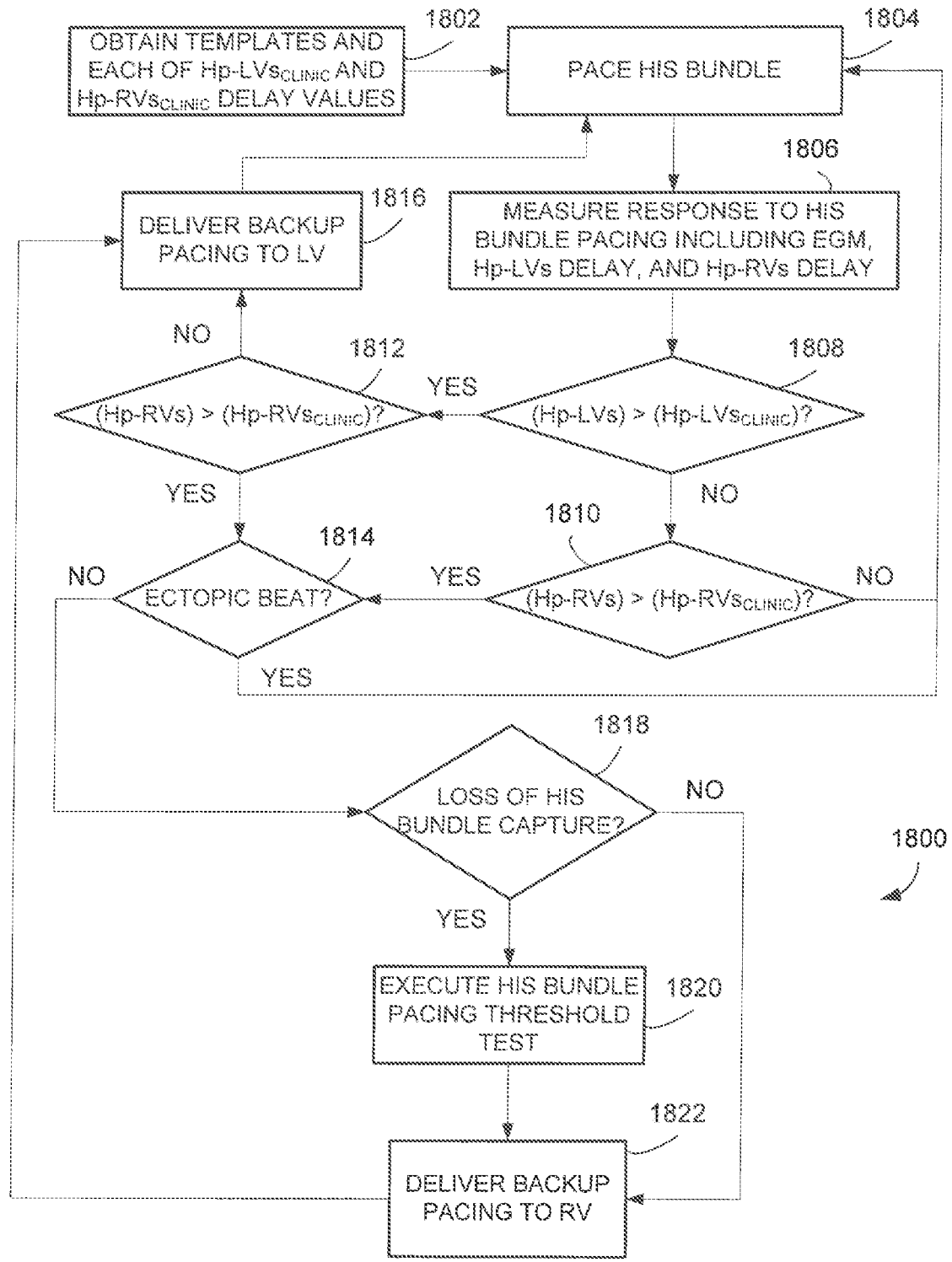
FIG. 18 is a flow chart illustrating a method for tracking and optimizing ventricular pacing delays that may be implemented using the stimulation system of FIG. 17.

Referring now to FIG. 18, a method 1800 for tracking and optimizing ventricular pacing delays is provided that may be implemented using the stimulation system 1700 of FIG. 17. Although the following description makes reference to the stimulation system 1700 and its various components, it should be appreciated that the method 1700 may be implemented using other stimulation system arrangements.

At operation 1802 the stimulation system 1700 obtains and stores templates, values, and other metrics for use in analyzing measured cardiac activity. In certain implementations, the stimulation system 1700 may store a set of templates corresponding to example QRS responses or metrics associated therewith, each template representing a particular cardiac event. The templates may include templates corresponding to, among other things, selective His bundle capture, non-selective His bundle capture, myocardium-only capture, non-capture, and intrinsic activation. In certain implementations, the templates may be programmed into the stimulation device 1700 after implantation such as during a clinical testing regimen. Generation of the templates may also be conducted as part of a threshold test, such as the threshold test illustrated in FIGS. 8A and 8B of the present disclosure. Once obtained, the templates are stored within a memory of the stimulation device.

For purposes of the current example, operation 1802 includes obtaining at least a first value (Hp-Ls$_{CLINIC}$) corresponding to the delay between pacing of the His bundle 1704 and pacing and depolarization of the LV 1708 and a second value (Hp-RVs$_{CLINIC}$) corresponding to the delay between pacing of the His bundle 1704 and depolarization of the RV 1722 as measured during clinical testing following implantation. As a result, Hp-LVs$_{CLINIC}$ and Hp-RVs$_{CLINIC}$ may provide baselines for the delay between His bundle pacing and depolarization of the LV 1708 and the RV 1722 against which subsequently measured delays may be measured. In certain implementations including multipolar leads for either the LV 1708 or the RV 1722, such values may be obtained for each electrode of the multipolar lead. In the example stimulation system 1700 of FIG. 17, for example, a set of Hp-LVs$_{CLINIC}$ values may be obtained, with at least one value corresponding to each of D1 1710, M2 1712, M3 1714, and P4 1716. In implementations in which a multipolar lead is used, Hp-LV$_{CLINIC}$ may also correspond to, among other things, a shortest or longest activation delay across all electrodes, a shortest or longest activation delay across a subset of electrodes, an average activation delay across some or all of the electrodes, or any other similar timing measurement.

At operations 1804 and 1806, the His bundle 1704 is paced and a corresponding response to the pacing of the His bundle 1704 is measured. As indicated in FIG. 18, the measured response may include an EGM measurement or similar waveform characterizing the electrical response of the heart 1701 to application of the His bundle pacing impulse in operation 1804. In certain implementations, the EGM measurement may be recorded by the stimulation device 1700 as a QRS waveform or as a set of values corresponding to particular characteristics of such a waveform. In addition to the EGM measurement, operation 1806 further includes measuring delays between pacing of the His bundle 1704 and each of depolarization of the LV 1708 (Hp-LVs) and depolarization of the RV 1722 (Hp-RVs). In implementations in which a multipolar lead is implemented, such values may be acquired each electrode of the corresponding lead and may be used to determine an activation order for the electrodes.

At operation 1808, a comparison is made between the stored delay value for the LV 1708 (i.e., Hp-LVs$_{CLINIC}$) and the delay measured between pacing of the His bundle 1704 and subsequent depolarization of the LV 1708 (i.e., Hp-LVs). If Hp-LVs does not exceed or is approximately equal to Hp-Ls$_{CLINIC}$, it may be assumed that the conduction paths related to the LV 1708 are in substantially the same condition as represented by Hp-LV$_{CLINIC}$. Regardless of the outcome of operation 1808, a similar comparison may then be made between the stored delay value for the RV 1722 (i.e., Hp-RVs$_{CLINIC}$) and the delay measured between pacing of the His bundle 1704 and subsequent depolarization of the RV 1722 (i.e., Hp-RVs) (operations 1810 and 1812). If Hp-RVs does not exceed or is approximately equal to Hp-RVs$_{CLINIC}$, it may be assumed that the current conduction paths related to the RV 1722 are in substantially the same condition as those represented by Hp-RVs$_{CLINIC}$. Accordingly, if both Hp-LVs and Hp-RVs are less than their respective clinically measured values (or similar threshold values stored in the stimulation device 1700), the stimulation device 1700 may restart the process of applying a pacing impulse to the His bundle 1704 (operation 1804) and measuring and assessing the resulting response (operations 1806-1812).

If, on the other hand, at least one of Hp-LVs is found to exceed Hp-LVs$_{CLINIC}$ or Hp-RVs is found to exceed Hp-RVs$_{CLINIC}$, the stimulation device 1700 may automatically take various additional steps. For example, as illustrated in FIG. 18, if Hp-LVs is found to exceed Hp-LV$_{CLINIC}$ but Hp-RVs is less than Hp-RVs$_{CLINIC}$, the stimulation device 1700 may deliver a backup pace to the LV 1708 (operation 1816) before resuming pacing of the His bundle (operation 1804).

If, on the other hand if Hp-RVs is found to exceed Hp-RVs$_{CLINIC}$ regardless of the outcome of the comparison of Hp-LVs to Hp-LVs$_{CLINIC}$, the stimulation device 1700 may determine whether the measured response corresponds to an ectopic beat (operation 1814). As previously discussed in the context of FIG. 16, determining whether a given beat is ectopic may include the stimulation device 1700 analyzing an electrode activation order, comparing the measured response to one or more templates, or similar operations. If the measured response represents or likely represents an ectopic beat, the stimulation device 1700 may again return to pacing of the His bundle 1704 using the current device settings (operation 1804).

However, if the beat is not ectopic, the stimulation device 1700 may further determine whether the measured response indicates a loss of His bundle capture (operation 1818). If so, the stimulation device 1700 may execute a His bundle pacing threshold test (operation 1820) or a similar reconfiguration routine (for example, as described above in the context of operation 1616 of FIG. 16) to adjust the settings of the stimulation device 1700 to recapture the His bundle 1704. Regardless of whether His bundle capture has been lost, the stimulation device 1700 may deliver a backup pacing pulse to each of the RV 1722 (operation 1822) and the LV 1708 (operation 1816) before resuming pacing of the His bundle 1704 (operation 1804).

Although not included in FIG. 18, the stimulation device 1700, like the stimulation device 1500 described in the context of FIGS. 15 and 16, may include logging functionality to record information regarding the functioning of the stimulation device 1700, the occurrence of particular events (e.g., ectopic beats or loss of His bundle capture), and the like during operation of the stimulation device 1700. Such log entries may be obtained and analyzed or otherwise assessed by a physician or technician to identify changes in the patient's condition, changes in the functioning of the stimulation system 1700, or other similar trends in the interaction between the patient and the stimulation system 1700 which may inform additional interventions.

As previously noted, backup pacing of the ventricles may be provided by the stimulation device when the delay between pacing of the His bundle and sensing of depolarization of a ventricle exceeds a threshold or similar value stored in the memory of the stimulation device. To efficiently pace the ventricle, such backup pacing may be provided after a delay that is less than the stored delay (e.g., Hp-LVs$_{CLINIC}$ or Hp-RVs$_{CLINIC}$). In other words, when ventricular pacing is provided, efficient pacing of the ventricle (e.g., the LV) may require the delay between pacing of the His bundle and pacing of the ventricle (e.g., for the LV, the H$_P$-LV$_P$ delay) should be less than the stored delay corresponding to pacing of the His bundle and sensing of the ventricle (e.g., for the LV, the H$_P$-LVs$_{CLINIC}$ delay). To facilitate such pacing impulse timing, the stimulation device may be configured to toggle between a first mode in which only His bundle pacing is provided and a second mode in which both His bundle pacing and ventricular pacing is provided.

In such implementations, the stimulation device may, when operating in the first mode, pace the His bundle and measure corresponding responses of the heart. If the delay between pacing of the His bundle and depolarization of a ventricle exceeds a first delay, the stimulation device may provide a backup impulse and enter into the second mode. The first delay may, for example, be a delay determined in-clinic for selective His bundle capture. When in the second mode, the stimulation device may automatically pace the His bundle then the ventricle after a second delay from pacing of the His bundle, the second delay being less than the first delay. The second delay may be gradually increased until it equals the first delay. At that time, ventricular pacing may be deactivated such that the stimulation device returns to operating in the first mode, as described above.

Figure 19:
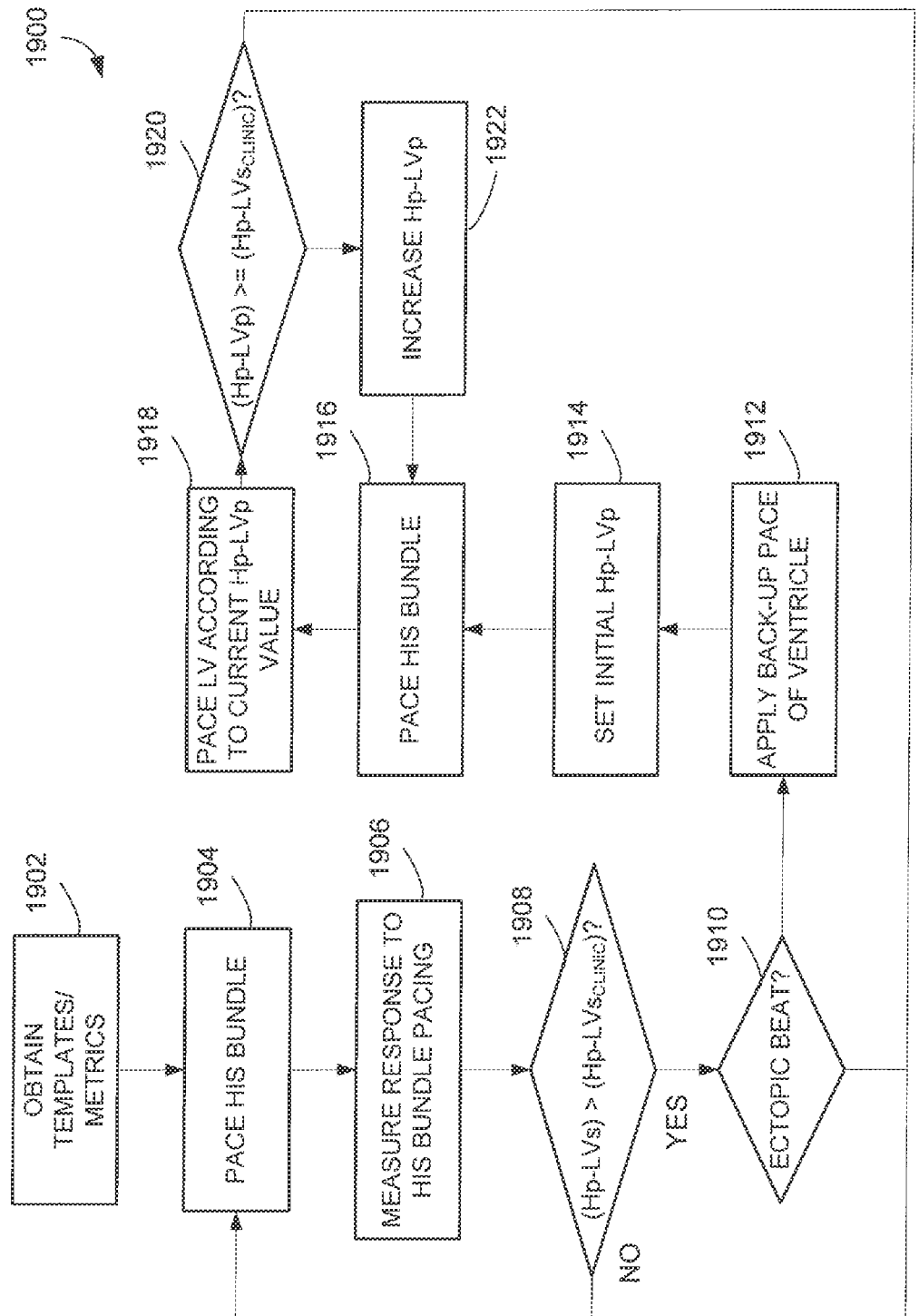
FIG. 19 is a flow chart illustrating an example method for tracking and optimizing pacing delays for pacing provided by a stimulation system.

FIG. 19 is a flow chart illustrating an example method 1900 for controlling a stimulation device. The method 1900 generally includes pacing of the His bundle and, based on the effects of such pacing, toggling between a first mode in which pacing of the His bundle continues according to the current settings of the stimulation device and a second mode in which pacing is applied to both the His bundle and one or more of the ventricles. For simplicity, the example method 1900 includes a second mode in which pacing is applied to the LV only; however, it should be appreciated that other implementations of methods in accordance with this disclosure may include pacing of one or both of the LV and RV.

At operation 1902, templates or metrics are obtained by the stimulation device. As previously discussed, the templates or metrics may include thresholds or similar values for delays between His bundle pacing and sensing of ventricular depolarization and example QRS responses or metrics associated therewith corresponding to different cardiac activity. The templates may include templates corresponding to, among other things, selective His bundle capture, non-selective His bundle capture, myocardium-only capture, non-capture, and intrinsic activation. In certain implementations, the templates may be programmed into the stimulation device after implantation, such as during a clinical testing regimen. Generation of the templates may also be conducted as part of a threshold test, such as the threshold test illustrated in FIGS. 8A and 8B of the present disclosure. Once obtained, the templates are stored within a memory of the stimulation device. For purposes of the current example, operation 1902 includes obtaining at least one value (Hp-LVs$_{CLINIC}$) corresponding to the delay between His bundle pacing and depolarization of the LV as measured during clinical testing following implantation. As a result, Hp- $LVs_{CLINIC}$ provides a baseline for the delay between His bundle pacing and depolarization of the LV against which subsequently measured delays may be measured.

At operations 1904 and 1906, the His bundle is paced and a corresponding response to the pacing of the His bundle is measured. In the example method 1900, the response includes a delay between the pacing of the His bundle and resulting depolarization of the LV (Hp-LVs). It should be appreciated that measurements obtained in response to pacing of the His bundle may include multiple measurements for a single chamber of the heart. For example, the stimulation device may include a multipolar lead having multiple electrodes, each of which may be used to measure a respective response to pacing of the His bundle.

At operation 1908, Hp-LVs is compared to Hp-$LVs_{CLINIC}$ as stored within the memory of the stimulation device. More specifically, the stimulation device determines if Hp-LVs exceeds Hp-$LVs_{CLINIC}$, which may indicate a reduction in conduction through the heart. Such a reduction in conduction may be attributable to, among other things, development of progressive conduction tissue disease, dislodgement or tissue buildup around a pacing electrode, to other changes within the heart that impact conduction.

If Hp-LVs is less than or equal to Hp-$LVs_{CLINIC}$, the general process of pacing the His bundle and analyzing corresponding responses is repeated. If, on the other hand, Hp-LVs is measured to be greater than Hp-$LVs_{CLINIC}$, a check may be performed to see if the measured response corresponds to an ectopic beat (operation 1910). For example, as previously described, such a check may be performed by comparing activation order of electrodes of a multipolar lead or comparing a measured QRS morphology with a template. If the beat is ectopic, the process of pacing the His bundle and analyzing the corresponding response is started over again. Accordingly, operations 1904-1910 generally corresponds to a first mode in which pacing is provided for the His bundle only.

However, if the beat is not ectopic, the stimulation device may apply a back-up pacing impulse to the LV (operation 1912) and begin a second mode of operation in which LV pacing occurs. For example, initializing the second mode may include initializing a LV pacing delay (Hp-LVp) (operation 1914). In certain implementations, the initial value for Hp-LVp is set to be less than Hp-$Ls_{CLINIC}$ to provide efficient pacing. For example and without limitation, Hp-LVp may be set to any of 50%-90% of Hp-$LV_{CLINIC}$. Alternatively, Hp-LVp may be set to be a specific time less than Hp-$LVs_{CLINIC}$. For example, and without limitation, Hp-LVp may be set to any of 5-30 ms less than Hp-$LV_{CLINIC}$.

Following initialization, the stimulation device paces the His bundle (operation 1916) followed by the LV after the current Hp-LVp delay (operation 1918). If the current setting for Hp-LVp is less than Hp-$LVs_{CLINIC}$ (as checked at operation 1920), the stimulation device may increase Hp-LVp (operation 1922) such that the difference between Hp-LVp and Hp-$LVs_{CLINIC}$ is decreased. The process of pacing the His bundle (operation 1916) and pacing the LV according to the current value of Hp-LVp (operation 1918) is then repeated until Hp-LVp equals or exceeds Hp-$LVs_{CLINIC}$. The amount by which Hp-LVp is increased each iteration and, as a result, the number of iterations may vary in implementations of the present disclosure. When Hp-LVp equals or exceeds Hp-$LVs_{CLINIC}$, LV pacing ceases and the stimulation device is returned to the first mode in which His bundle pacing only is provided by the stimulation device (operation 1904).

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present disclosure. References to details of particular embodiments are not intended to limit the scope of the disclosure.

What is claimed is:

1. A method of providing pacing to a patient's heart using a stimulation device, the method comprising:
   applying an impulse to a His bundle of the patient's heart using the stimulation device;
   measuring, using the stimulation device, a response of the patient's heart to the application of the impulse, the response including a response of a ventricle of the patient's heart;
   calculating a ventricular delay, the ventricular delay being a time from the application of the impulse to onset of the response of the ventricle; and
   delivering, using a lead of the stimulation device, a backup impulse to the ventricle when at least the ventricular delay exceeds a delay value stored in a memory of the stimulation device.

2. The method of claim 1 further comprising determining when the response corresponds to an ectopic beat of the patient's heart, wherein the backup impulse is delivered when the response does not correspond to an ectopic beat and is not delivered when the response corresponds to the ectopic beat.

3. The method of claim 1, wherein the lead comprises a plurality of electrodes and the ventricular delay is one of a plurality of ventricular delays, each of the ventricular delays measured using a respective one of the plurality of electrodes.

4. The method of claim 3 further comprising determining a conduction order of the plurality of electrodes based on the plurality of delays, wherein determining the response does not correspond to an ectopic beat of the patient's heart comprises determining the conduction order is consistent with a predetermined conduction order stored in the memory of the stimulation device.

5. The method of claim 2, wherein determining the response does not correspond to an ectopic beat of the patient's heart comprises comparing the response to a response template stored within the memory of the stimulation device.

6. The method of claim 1 further comprising determining the impulse did not result in capture of the His bundle and, in response to determining the impulse did not result in capture of the His bundle, modifying a pacing parameter of the stimulation device such that at least one of an amplitude, a duration, or a timing of a subsequent impulse is different from that of the impulse applied to the His bundle.

7. The method of claim 1, wherein the ventricle is a left ventricle and the response further includes a response of a right ventricle (RV) of the patient's heart, the method further comprising:

calculating a RV delay, the RV delay being a time from application of the impulse to onset of the response of the RV; and delivering, using a RV lead of the stimulation device, a RV backup impulse to the RV when at least the RV ventricular delay exceeds a RV delay value stored in the memory of the stimulation device.

8. The method of claim 1, wherein the backup impulse is delivered after a backup delay, the backup delay being less than the delay value stored in the memory of the stimulation device.

9. The method of claim 1, wherein one or more subsequent backup impulses are provided using respective and increasing backup delays until the backup delay of a one of the subsequent backup impulses exceeds the delay value stored in the memory of the stimulation device.

10. A method of pacing a patient heart using a stimulation device, the method comprising:

applying an impulse to a His bundle of the patient's heart using the stimulation device;

measuring, using the stimulation device, a response of the patient's heart to application of the impulse, the response including a response of a ventricle of the patient's heart;

calculating a ventricular delay, the ventricular delay being a time from application of the impulse to onset of the response of the ventricle; and entering a backup pacing mode of the stimulation device at least when the ventricular delay exceeds a delay value stored in the memory of the stimulation device, wherein in the backup pacing mode a backup impulse is applied to the ventricle by the stimulation device.

11. The method of claim 10, wherein when in the backup pacing mode, the backup impulse is applied to the ventricle after a backup delay measured from pacing of the His bundle, the backup delay being less than the delay value stored in the memory of the stimulation device.

12. The method of claim 11, wherein the backup delay is a first backup delay and at least one subsequent backup impulse is applied to the ventricle by the stimulation device, the at least one subsequent backup impulse delivered after a second backup delay that is greater than the first backup delay.

13. The method of claim 11, wherein entering the backup pacing mode further requires determining the response of the ventricle does not correspond to an ectopic beat.

14. A stimulation device for use in applying His bundle pacing of a patient's heart, the stimulation device comprising:

a housing containing a memory and a controller;

a His bundle lead coupleable to each of the housing and the patient's heart and a His bundle of the patient's heart; and a ventricular lead coupleable to each of the housing and a ventricle of the patient's heart;

wherein the controller is configured to:

apply, through the His bundle lead, a pacing impulse to the His bundle;

measure, using the ventricular lead, a response of the patient's heart to application of the impulse, the response including a response of the ventricle;

calculate a ventricular delay, the ventricular delay being a time from application of the pacing impulse to onset of the response of the ventricle; and apply, using the ventricular lead, a backup impulse to the ventricle when at least the ventricular delay exceeds a delay value stored in the memory.

15. The stimulation device of claim 14, wherein the ventricular lead is a left ventricle (LV) lead, the ventricle is a LV of the patient's heart, and the stimulation device further comprises a right ventricle (RV) lead, the controller further configured to:

measure, using the RV lead, the response of the patient's heart to application of the impulse, the response including a response of the RV;

calculate an RV delay, the RV delay being a time from application of the pacing impulse to onset of the response of the RV; and apply, using the RV lead, a RV backup impulse to the RV when at least the RV delay exceeds a RV delay value stored in the memory.

16. The stimulation device of claim 14, wherein the controller is further configured to determine the response does not correspond to an ectopic beat of the patient's heart and to apply the backup impulse when the response does not correspond to an ectopic beat.

17. The stimulation device of claim 14, wherein the ventricular lead comprises a plurality of electrodes and the ventricular delay is one of a plurality of ventricular delays, each of the ventricular delays measured using a respective one of the plurality of electrodes, the controller further configured to determine an activation order of the plurality of electrodes.

18. The stimulation device of claim 14, wherein the controller is further configured to determine the impulse did not result in capture of the His bundle and, in response to determining the impulse did not result in capture of the His bundle, automatically modify a pacing parameter for a subsequent impulse applied to the His bundle.

19. The stimulation device of claim 14, wherein the controller is configured to apply the backup impulse after a backup delay, the backup delay being less than the delay value stored in the memory of the stimulation device.

20. The stimulation device of claim 14, wherein the controller is further configured to apply one or more subsequent backup impulses after a backup delay and to increase the backup delay between backup impulses until the backup delay exceeds the delay value stored in the memory of the stimulation device.

* * * * *